US008278871B2

(12) United States Patent
Kallmyer

(10) Patent No.: US 8,278,871 B2
(45) Date of Patent: Oct. 2, 2012

(54) OPEN-LOOP RECHARGE FOR AN IMPLANTABLE MEDICAL DEVICE

(75) Inventor: Todd A. Kallmyer, Tempe, AZ (US)

(73) Assignee: Medtronic, Inc., Minneapolis, MN (US)

( * ) Notice: Subject to any disclaimer, the term of this patent is extended or adjusted under 35 U.S.C. 154(b) by 845 days.

(21) Appl. No.: 12/417,824

(22) Filed: Apr. 3, 2009

(65) Prior Publication Data
US 2010/0256709 A1    Oct. 7, 2010

(51) Int. Cl.
    *H02J 7/00* (2006.01)
(52) U.S. Cl. .................... 320/108; 320/139; 607/61
(58) Field of Classification Search .............. 324/108
    See application file for complete search history.

(56) References Cited

U.S. PATENT DOCUMENTS

| | | | |
|---|---|---|---|
| 6,415,186 B1 | 7/2002 | Chim et al. | |
| 6,518,731 B2* | 2/2003 | Thomas et al. | 320/136 |
| 6,608,470 B1* | 8/2003 | Oglesbee et al. | 320/136 |
| 7,254,449 B2 | 8/2007 | Karunasiri | |
| 7,286,880 B2 | 10/2007 | Olson et al. | |
| 2005/0288739 A1 | 12/2005 | Hassler et al. | |
| 2009/0005770 A1 | 1/2009 | Gerber et al. | |
| 2009/0132188 A1* | 5/2009 | Watanabe | 702/64 |

FOREIGN PATENT DOCUMENTS

WO    2008151059 A2    12/2008

OTHER PUBLICATIONS

PCT International Search Report and Written Opinion dated May 25, 2010.

* cited by examiner

*Primary Examiner* — Jay Patidar
(74) *Attorney, Agent, or Firm* — Beth L. McMahon

(57) ABSTRACT

Techniques for recharging a rechargeable power source coupled to a secondary coil implanted within a living body are described. In one embodiment, a recharging device external to the living body induces a sequence of pulses in a primary coil that is coupled to the secondary coil. The sequence includes high-amplitude pulses alternating with low-amplitude pulses, each high-amplitude pulse having an amplitude selected to transfer charge to the rechargeable power source during times of poor coupling between the primary coil and the secondary coil, each low-amplitude pulse having an amplitude selected to transfer charge to the rechargeable power source during times of good coupling between the primary coil and the secondary coil, and wherein the sequence of pulses is selected to prevent a violation of a limiting condition such as heating that is associated with recharging the rechargeable power source when recharging occurs in an open-loop manner.

31 Claims, 9 Drawing Sheets

OPEN-LOOP RECHARGE FOR AN IMPLANTABLE MEDICAL DEVICE

FIELD OF THE INVENTION

This invention relates to implantable medical devices and, in particular, to energy transfer devices, systems and methods for implantable medical devices.

BACKGROUND OF THE INVENTION

Implantable medical devices for producing a therapeutic result in a patient are well known. Examples of such implantable medical devices include implantable drug infusion pumps, implantable neurostimulators, implantable cardioverters, implantable cardiac pacemakers, implantable defibrillators and cochlear implants. Of course, it is recognized that other implantable medical devices are envisioned which utilize energy delivered or transferred from an external device.

A common element in all of these implantable medical devices is the need for electrical power in the implanted medical device. The implanted medical device requires electrical power to perform its therapeutic function, which may include driving an electrical infusion pump, providing an electrical neurostimulation pulse or providing an electrical cardiac stimulation pulse. This electrical power is derived from a power source.

In some implantable medical devices electrical power can be transcutaneously transferred through the use of inductive or RF coupling. For instance, this can be accomplished by inductively coupling a primary coil that is external to a living body with a secondary coil that is coupled to, or included within, the implantable medical device. Current induced in the secondary coil is used to store energy in a rechargeable battery or capacitive element and/or to power the implantable medical device implanted within the body. In this form, an internal power source such as battery or capacitive element can be used for direct electrical power to the implanted medical device. When the power source has expended, or nearly expended, its capacity, the power source can be again recharged transcutaneously via inductive coupling from an external power source that drives a primary coil that is temporarily positioned on the surface of the skin.

Devices and techniques have been developed to provide transcutaneous energy transfer in order to power an implantable medical device and/or charge or recharge a battery associated with an implantable medical device. As previously noted, techniques generally employ a primary coil driven by an external power source.

BRIEF SUMMARY OF THE INVENTION

A recharging device for recharging a power source of implantable medical devices (IMDs) is disclosed. The recharging device charges a rechargeable power source of an IMD in an open-loop mode, without receiving any feedback from the IMD concerning how energy transfer is occurring between the recharging device and the IMD.

According to one aspect of open-loop recharging, the recharging device drives a primary coil with a short, high-amplitude pulse that is capable of transferring enough power to a secondary coil of the IMD so that some charge will be transferred to the rechargeable power source even if coupling between the primary and secondary coils is poor. This high-amplitude pulse must be sufficiently short to prevent violation of a limiting condition of the IMD. As discussed further below, this limiting condition may involve a temperature limit associated with one or more circuit components and/or heating of the can of the IMD.

After delivery of this high-amplitude pulse, a first delay is initiated to allow cooling to occur. The recharging device then drives the primary coil with a low-amplitude pulse that will cause charge to flow to the rechargeable power source at a rate that will accomplish efficient recharge if coupling between the primary and secondary coils is good. Like the high-amplitude pulse, this low-amplitude pulse must be short enough to prevent violation of the limiting condition.

Following delivery of the low-amplitude pulse, a second delay is initiated to again allow cooling to occur. After this second delay has elapsed, another high-amplitude pulse may be delivered and the sequence of pulses and delays is repeated. In this manner, a series of pulses is generated in the primary coil that includes high-amplitude pulses alternating with low-amplitude pulses. The pulses are sized to prevent violation of a limiting condition of the IMD when recharge occurs in open-loop mode. This is important, since in open-loop mode, the IMD does not provide feedback concerning heating of elements within the IMD, or information concerning the state of the power source.

In one embodiment, a limiting condition may involve overheating of circuit components within the IMD. Such overheating of the IMD may be caused, for instance, if the high-amplitude pulse is delivered at a time when optimal (best-case) coupling exists between the primary and secondary coils, and the rechargeable power source is topped-off so that it cannot receive additional charge. In such circumstances, most, or all, of the flow of charge generated in the secondary coil by the primary coil must be diverted away from the rechargeable power source. This diversion may occur via a shunting element, for instance. This shunting element may overheat if the pulse is not sized appropriately.

To prevent overheating of the shunting element, the width of the high-amplitude pulse is selected so that a high-temperature limit associated with the limiting condition is not exceeded. The sizing of the pulse may be determined using a temperature coefficient $\tau$ that is associated with the limiting condition. In this specific example, the temperature coefficient may be that associated with the shunting element and the related circuit. This temperature coefficient may be used to calculate the maximum width of the high-amplitude pulse that may be safely delivered without causing the selected high-temperature limit to be exceeded. The width of the pulse may also be determined based on a low-temperature limit, which is a temperature existing at the beginning of delivery of the high-amplitude pulse. Either or both of the high and low temperature limits may be programmable.

As is the case with the high-amplitude pulse, the low-amplitude pulse may likewise cause violation of the limiting condition. For instance, in one embodiment, if the low-amplitude pulse is delivered at a time when optimal coupling exists between the primary and second coils and the rechargeable power source is in the topped-off state, the flow of charge resulting from the low-amplitude pulse must be diverted. The width of the low-amplitude pulse must be selected so that a high-temperature limit associated with this pulse is not exceeded. Again, the determination regarding this width is made using the temperature coefficient of the system. The width of the low-amplitude pulse is further determined by low and high temperature limits associated with this pulse. As described above, these temperatures are associated with the beginning and end of delivery of the low-amplitude pulse, respectively.

While the foregoing discusses the limiting condition as being associated with a shunting element, other conditions may limit the amount of power transfer to the secondary coil. For instance, in other systems, the limiting condition may involve the temperature of the secondary coil and/or the temperature of the rechargeable power source during times when coupling between the primary and secondary coils is of a selected quality (which may be optimal, or something other than optimal). Thus, the foregoing example of using temperature of the shunting element during optimal coupling when the rechargeable power source is in a topped-off state is only one example of a limiting condition.

According to another aspect, after delivery of each high-amplitude pulse, a first delay is initiated that is selected to have a length that will allow a transition to take place involving the limiting condition. In one embodiment, this involves allowing a temperature associated with the shunting element to transition from a high-temperature limit for the high-amplitude pulse to a low-temperature limit of a next low-amplitude pulse. After this transition has occurred, a subsequent low-amplitude pulse may be delivered.

In a similar manner, after delivery of each low-amplitude pulse, a second delay is initiated that is adequate to allow a transition to occur involving the limiting condition. In one embodiment, this involves allowing a temperature associated with the shunting element to transition from a high-temperature limit of the low-amplitude pulse to a low-temperature limit of the next high-amplitude pulse.

Many methods are possible to select the pulse amplitudes. In one embodiment, an amplitude of the low-amplitude pulse is selected to be that which will cause a selected flow of charge to the rechargeable power source. In one particular embodiment, the low-amplitude pulse is selected to be that which will cause a flow of charge to the rechargeable power source that is the maximum flow of charge that can be stored by the rechargeable power source when the rechargeable power source is not topped off and good coupling exists between the primary and secondary coil. When recharge is occurring in open-loop mode, if good coupling is achieved between the primary coil and the secondary coil, this low-amplitude pulse is selected to provide near-optimal recharge capability. However, this low-amplitude pulse may not provide any flow of charge to the rechargeable power source during times of poor coupling.

The high-amplitude pulse of one embodiment is selected to have an amplitude that will cause a selected flow of charge to the rechargeable power source during times of poor coupling. In one scenarios, the high-amplitude pulse is selected to be that which will cause at least some minimum flow of charge to the rechargeable power source that will be usefully employed to accomplished recharge during times of poor coupling.

In another embodiment, the amplitude of the high-amplitude pulse with which the primary coil is driven is selected as the maximum amplitude with which the recharging device is capable of driving the primary coil, and without regard to the rate of charge flow to the rechargeable power source. The amplitude of the low-amplitude pulse may then be selected based on some percentage of the amplitude selected for use with the high-amplitude pulse.

In yet another embodiment, the amplitude of the low-amplitude pulse may be selected as being that amplitude used to drive the primary coil during a typical recharge session, and the high-amplitude pulse may be an amplitude that is something higher than this typical power level, such as some multiple of this power level.

Thus, many techniques are possible for selecting amplitudes of the high- and low-amplitude pulses. Regardless of how the amplitudes for these pulses are selected, what is important is that once the amplitudes are selected, appropriate widths are chosen so that the pulses do not violate a limiting condition.

According to one aspect, a system is described that comprises a secondary coil implanted within a living body, and a rechargeable power source coupled to receive a flow of charge from the secondary coil. A recharging device external to the living body induces a sequence of pulses in a primary coil that is coupled to the secondary coil. The sequence includes high-amplitude pulses alternating with low-amplitude pulses, each high-amplitude pulse having an amplitude selected to result in transfer of charge to the rechargeable power source during times of poor coupling between the primary coil and the secondary coil, each low-amplitude pulse having an amplitude selected to result in transfer of charge to the rechargeable power source during times of good coupling between the primary coil and the secondary coil, and wherein the sequence of pulses is selected to prevent violation of a limiting condition associated with recharging the rechargeable power source when recharging occurs in an open-loop manner.

Another embodiment includes a system to recharge a rechargeable power source of an implantable medical device. The system comprises a power source, a primary coil to wirelessly couple to a secondary coil of the IMD, and a control unit to cause the power source to drive the primary coil with high-amplitude pulses and low-amplitude pulses. Each high-amplitude pulse is followed by a low-amplitude pulse and each low-amplitude pulse is followed by a high-amplitude pulse. Each high-amplitude pulse is of an amplitude selected to cause the secondary coil to provide charge to the rechargeable power source when poor coupling exists between the primary coil and the secondary coil. Each low-amplitude pulse is of an amplitude selected to cause the secondary coil to provide charge to the rechargeable power source when good coupling exists between the primary coil and the secondary coil.

Another aspect includes a system comprising an implantable medical device having a secondary coil and a rechargeable power source to receive charge from the secondary coil. Also included is a recharging device having a primary coil and a circuit to drive the primary coil with a sequence of pulses to perform open-loop recharge of the rechargeable power source. The sequence of pulses includes high-amplitude pulses alternating with low-amplitude pulses, each high-amplitude pulse being of a relatively high amplitude, each low-amplitude pulse being of a relatively low amplitude, and wherein none of the low-amplitude pulses and none of the high-amplitude pulses cause violation of a limiting condition that limits the manner in which the rechargeable power source may be recharged.

A method is also disclosed that includes wirelessly coupling a primary coil that is external to a living body to a secondary coil implanted in the living body. A sequence of pulses is generated in the secondary coil via this coupling. The sequence of pulses is for use in recharging a rechargeable power source that is coupled to the secondary coil. The sequence includes high-amplitude pulses alternating with low-amplitude pulses, the high-amplitude pulses each having an amplitude selected to deliver a flow of charge to the rechargeable power source when the coupling is of a first quality, the low-amplitude pulses each having an amplitude selected to deliver a flow of charge to the rechargeable power source when the coupling is of a second quality that is better than the first quality, and wherein the width of each of the high-amplitude and the low-amplitude pulses is selected to prevent violation of a limiting condition during open-loop recharge of the rechargeable power source.

Other aspects will become apparent from the following description and the accompanying drawings.

DETAILED DESCRIPTION OF THE INVENTION

Figure 1:
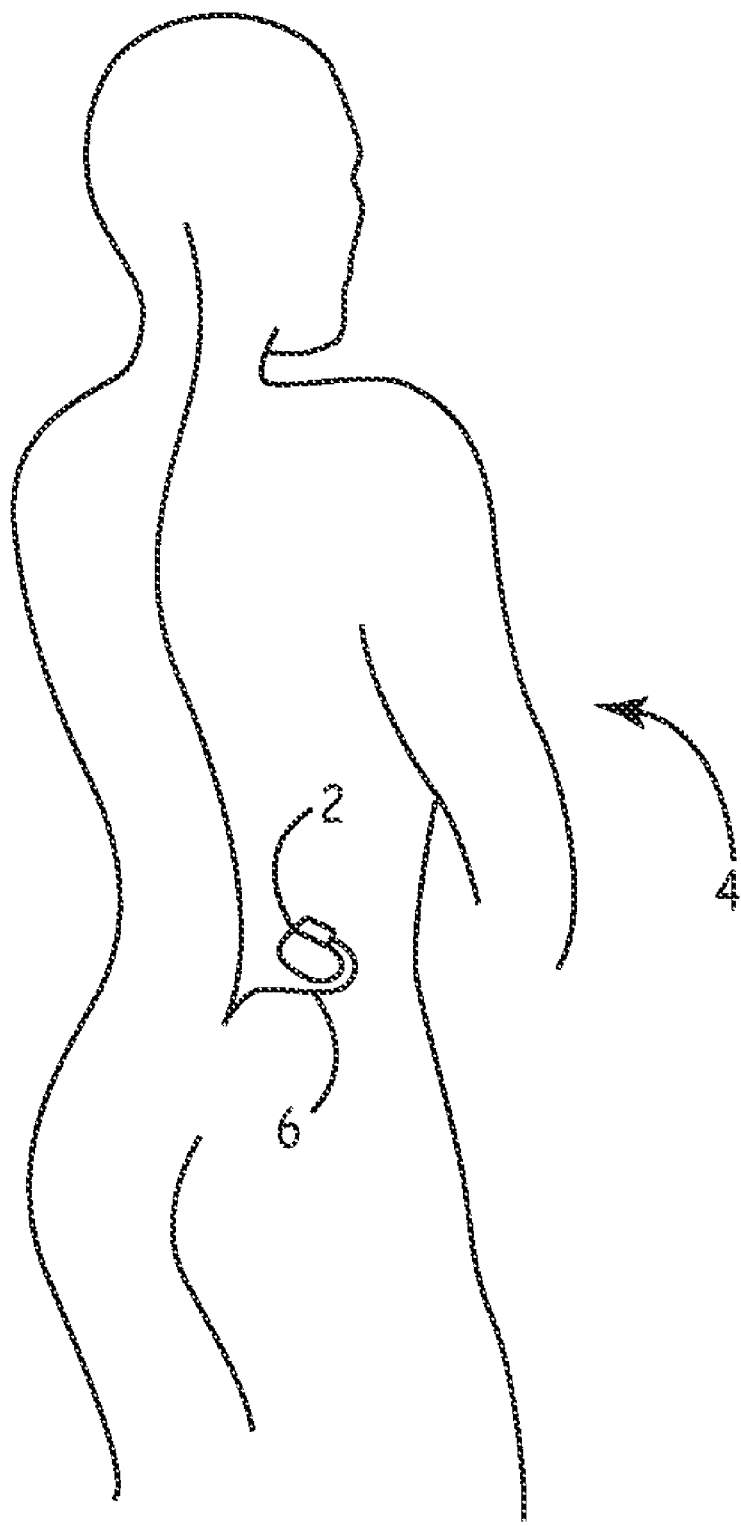
FIG. 1 is a system view of an exemplary Implantable Medical Device, which may be a neurostimulator, implanted in patient.

Techniques are disclosed for recharging a power source within an implantable medical device (IMD). One way to recharge a power source within an IMD is to provide a secondary coil within, or otherwise associated with, the IMD. This secondary coil may be inductively coupled to a primary coil that is external to the patient's body. In other embodiments, this coupling may be accomplished using RF energy. A current generated in the primary coil results in generation of a current in the secondary coil that may be used to recharge the rechargeable power source.

IMDs have varying types of secondary coils and rechargeable power sources. For instance, the size, shape, number of turns in the coil winding and/or orientation of the secondary coil within a particular IMD may vary according to IMD and therapy type. These variations will generally affect the amount of power that may be transferred from the primary coil to the secondary coil during a predetermined period of time.

Other factors will contribute to the amount of power that will be transferred from the primary coil to the secondary coil during a given time period. For instance, the distance between the primary coil and the secondary coil will affect the power transfer, as will the orientation of the secondary coil within the patient's body. Moreover, the ability of the patient to locate the primary coil in close proximity to the secondary coil will affect the efficiency of power transfer. If the patient is unable to accurately place the primary coil in proximity to the secondary coil, the current generated within the secondary coil may be relatively small, increasing the time needed to complete the recharge.

The amount of power transferred to the secondary coil should be controlled for several reasons. If too much power is transferred at a given time to the secondary coil (e.g., the current that is generated in the secondary coil is too large), the rechargeable power source will be unable to receive all of this power. Therefore, some of the power must be shunted away from the power source. This shunted power is wasted, and is dissipated as heat. The amount of this dissipated heat must be limited so that patient discomfort and even tissue damage does not result. The heating must also be limited to protect against damage to internal circuits of the device.

The amount of power that a power source may usefully absorb will vary depending on the state of charge of the power source. When the power source is nearing a fully-charged state, the power source will be capable of receiving less charge over a given period of time than a power source that is in a nearly-depleted state.

Exercising control over the rate at which power is transferred to the secondary coil is important for another reason. Typically, the life of the battery may be extended if the battery is recharged more slowly. This involves supplying the battery with power at a rate that is less than the maximum rate at which the power source can be recharged. While this will result in a recharge session that takes longer to complete, it will increase the time between the surgical procedures that are required to replace the battery.

For the foregoing reasons, it is generally desirable for the external recharging device to receive feedback from the IMD indicating the rate at which power is being transferred to the secondary coil by the primary coil. For instance, when the external recharging device initiates a recharge operation with the IMD, the IMD may provide an uplink communication indicating the degree of coupling between the primary and secondary coils, the amplitude of current being generated in the secondary coil, voltage across the secondary coil, or some other indication of the rate at which power is being transferred to the IMD. The external recharging device uses this feedback to adjust the power being provided to the primary coil. This prevents too much or too little power from being transferred from the primary coil to the secondary coil during a given time period. As an example, if the feedback indicates that the coupling efficiency is poor such that very little power is being transferred to the secondary coil, the external recharging device may begin driving the primary coil at a higher power level. Conversely, if the feedback from the IMD indicates that too much heat is being dissipated within the IMD and/or the power being transferred to the secondary coil is too great, the external recharging device may decrease the power being provided to the primary coil.

In some circumstances and/or systems, the type of feedback described above will not be available. For instance, in a scenario in which the power source of the IMD has been allowed to discharge to a level that is too low to enable a telemetry communication session to be established, no feedback will be provided by the IMD. Feedback will not be available until enough power has been supplied to the IMD to power the communication system of the IMD.

As another example, in some types of streamlined systems, telemetry circuitry may not be available to provide communication. This may be true in some very small microstimulation systems wherein size limitations preclude the use of such circuitry, for instance. Therefore, feedback is not available to control the power transfer from a primary to a secondary coil.

The current disclosure provides mechanisms for transferring power to an IMD without the use of feedback. The disclosed techniques allow the transfer of power to be sufficient to transfer power to a power source of an IMD in those situations wherein inductive or RF coupling is poor. However, in those situations wherein coupling is good, the rate of power transfer is not allowed to exceed that which will result in safe power dissipation within the IMD.

Before describing the specifics of the above-described techniques in more detail, a discussion is provided concerning an exemplary IMD that may employ the mechanisms described herein.

FIG. 1 shows an exemplary IMD 2, which may be a neurostimulator, implanted in patient 4. IMD 2 can be any number of medical devices such as an implantable therapeutic substance delivery device, an implantable drug pump, a cardiac pacemaker, a cardioverter or defibrillator, a device to deliver electrical stimulation pulses for a neurological or muscular condition, a device to deliver electrical stimulation to alleviate pain, or any other IMD for delivering therapy. This therapy may be delivered via one or more therapy connections 6, which may be one or more leads and/or catheters. The patient's body may carry additional IMDs which may be similar, or different from, IMD 2.

Figure 2:
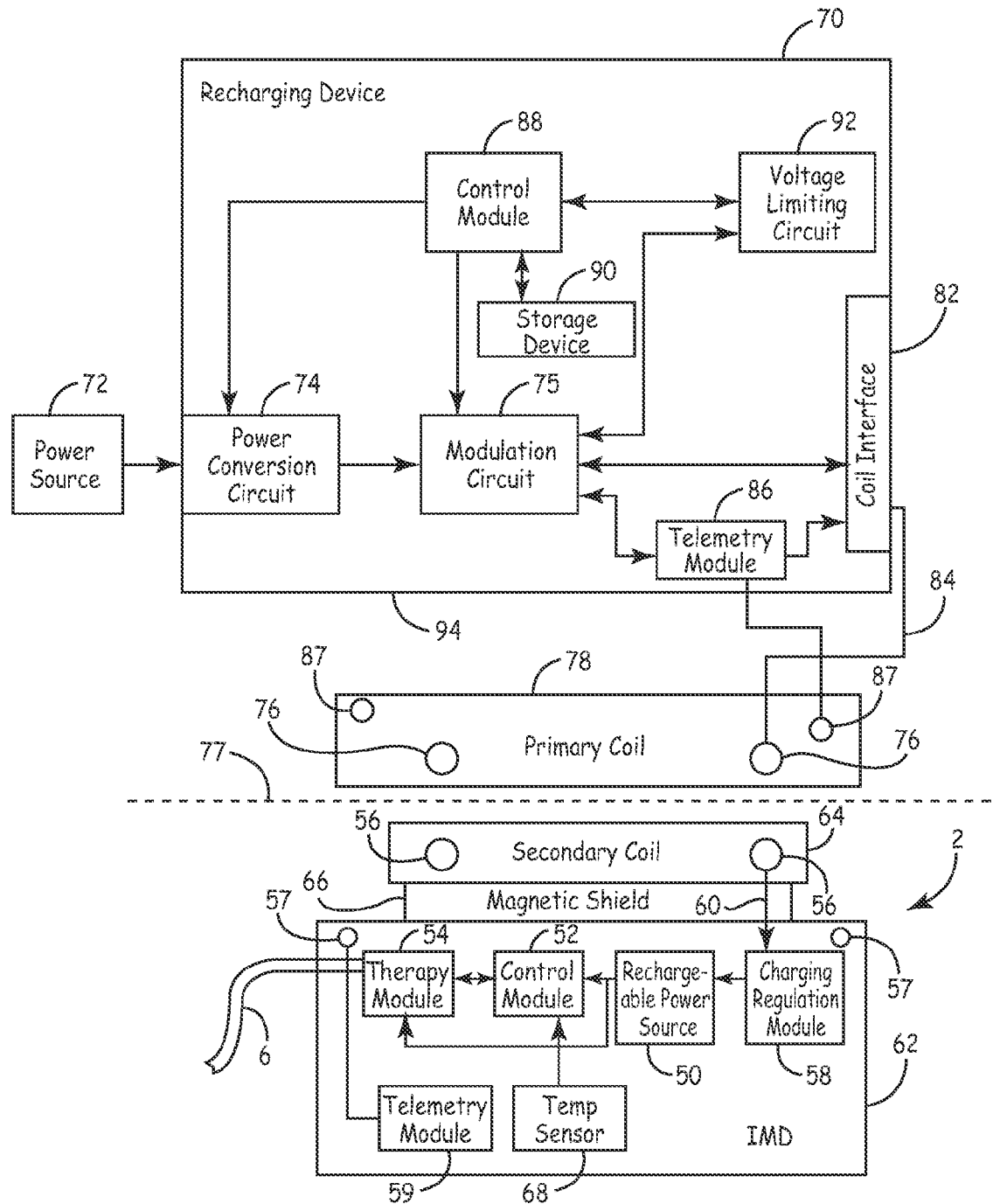
FIG. 2 is a block diagram of one embodiment of the Implantable Medical Device of FIG. 1 and a recharging device for recharging a power source of the Implantable Medical Device.

FIG. 2 is a block diagram of one embodiment of IMD 2 and recharging device for recharging a rechargeable power source 50 of the IMD. Rechargeable power source 50 may be any of a variety of rechargeable power sources including a chemically-based battery and/or one or more capacitive elements. In one embodiment, rechargeable power source 50 is a lithium ion battery. Any other type of rechargeable battery suitable for powering an IMD may be used.

Rechargeable power source 50 is coupled to a control module 52, which includes circuitry to control therapy delivered to the patient. Control module 52 may include one or more microprocessors, application-specific integrated circuits (ASICs), digital signal processors (DSPs), field-programmable gate arrays (FPGAs), discrete electronic components, state machines, sensors, storage devices for storing programmed instructions and/or other circuitry.

Control module 52 is further coupled, and provides power, to therapy module 54. Therapy module 54 delivers some form of therapy to a patient. This therapy may include controlled delivery of a substance and/or electrical stimulation. For example, in one embodiment, therapy module 54 may include one or more output pulse generators such as capacitive elements, voltage regulators, current sources, and/or switches that are coupled to rechargeable power source 50 directly or through control module 52. Therapy module 54 may deliver electrical pulses to patient 4 via a combination of electrodes. Therapy module 54 is coupled to patient 2 through one or more therapy connections 6 such as leads and/or catheters.

In one embodiment, rechargeable power source 50 is coupled to a secondary coil 56 (shown in cross-section) through a charging regulation module 58. During a recharge session, a current is induced in secondary coil 56. This current is provided via connection 60 to charging regulation module 58, which controls the charging of rechargeable power source 50. IMD 2 may optionally include a telemetry module 59 coupled to a telemetry coil 57 (shown in cross-section). Telemetry coil 57 and telemetry module 59 may utilize various types of telemetry protocols to communicate with external recharging device 70. A proximal telemetry system is utilized for telemetry distances of 5 centimeters or less. An arm's length telemetry system is employed for distances of up to 1 meter. This latter type of system may utilize E-field transmission (e.g., the MICS band set aside for medical device telemetry.) Arm's length telemetry may also be achieved using H-field or coupled-coil transmission.

Rechargeable power source 50, charging regulation module 58, control module 52, therapy module 54, telemetry module 59 and telemetry coil 57 may be contained in a hermetically sealed housing 62. Secondary coil 56 may be attached to, or positioned on, an exterior surface of sealed housing 62 through connection 60. For instance, secondary coil 56 may be contained within a second housing 64 that is positioned adjacent to sealed housing 62. In an alternative embodiment, secondary coil 56 may be contained in housing 62 along with the other electronics.

In one embodiment, a magnetic shield 66 may be positioned between secondary coil 56 and housing 62. The primary purpose of magnetic shield 66 is to substantially increase the amount of energy captured by the secondary coil. Magnetic shield 66 also protects rechargeable power source 50, control module 52, therapy module 54 and charging regulation module 58 from electromagnetic energy when secondary coil 56 is utilized to charge rechargeable power source 50.

In one embodiment, IMD 2 includes a temperature sensor 68. This sensor senses the temperature associated with one or more components within the IMD. For instance, temperature sensor 68 may sense the temperature of secondary coil 56, the temperature of rechargeable power source 50, the temperature of a power shunting element (not shown in FIG. 2) and/or the temperature of one or more other elements within, or otherwise associated with, IMD 2. This will be discussed further below.

FIG. 2 further illustrates one embodiment of a recharging device 70 for recharging rechargeable power source 50. Recharging device 70 is coupled to a power source 72, which may be a source of AC power, such as a standard wall outlet. In another embodiment, power source 72 may be a battery, thereby allowing recharging device to be portable so that a patient may recharge rechargeable power source 50 of IMD 2 while going about a daily routine. For instance, in this case, power source 72 may include lithium ion rechargeable batteries. Such batteries can be packaged in thin, flexible foil packs. Lithium ion batteries would have to be recharged. This may be accomplished by placing the batteries, or in some embodiments, the entire recharging device 70, in a recharge cradle or some other recharging system. In other embodiments, the batteries may be non-rechargeable primary-cell batteries.

Power received from power source 72 such as a wall outlet or a battery is received by power conversion circuit 74, which supplies appropriate power to modulation circuit 75. Modulation circuit 75 includes a frequency generator to generate a recharge signal, typically somewhere between 8 kilohertz and 500 kilohertz. The recharge signal may be a sine wave or some other type of signal, if desired. The frequency of the recharge signal may depend on the resonant frequency of the system, which takes into account the loading placed on the system when secondary coil 56 is inductively coupled or coupled via RF energy across cutaneous boundary 77 (shown dashed) to primary coil 76 housed in antenna 78. Recharging device 70 may vary the frequency during a charging session to find the most optimal frequency for charging efficiency.

The signal generated by modulation circuit 75 is provided to coil interface 82 which drives primary coil 76 via interconnection 84. Primary coil 76 may be of many different configurations (e.g., shapes, sizes, and including any number of turns). The configuration of primary coil 76 may be selected based on the size and shape of secondary coil 56, as well as the implant scenario associated with IMD 2. For instance, if IMD 2 is intended for use in a deep implant scenario, it may be desirable to configure primary coil 76 to include a large number of coil turns, since this will result in the generation of a larger magnetic field, which will be needed to achieve adequate coupling at the greater implant depth. This may likewise be true if primary coil 76 is intended for placement at some distance from cutaneous boundary 77 instead of directly on cutaneous boundary, as may be applicable for some implant scenarios, such as when an insulator or a cooling device is positioned between the primary coils 76 and the cutaneous boundary.

Recharging device 70 may have a telemetry module 86 enabling recharging device 70 to be in communication with IMD 70. Telemetry module 86 may be adapted to utilize various types of telemetry protocols, including a proximal protocol for telemetry distances of 5 centimeters or less and an arm's-length telemetry protocol for distances of up to 1 meter. In one embodiment telemetry module 86 may communicate via a dedicated telemetry coil 87 (shown in cross-section) within antenna 78. In another embodiment, telemetry module 86 may instead drive primary coil 76 to provide downlink communication to IMD 2, rather than driving a dedicated telemetry coil for this purpose.

Operation of charging device 70 may be controlled by control module 88, which may include one or more microprocessors, FPGAs, ASICs, DSPs, microsequencers, discrete components, storage devices storing programmed instructions and/or other electronic circuit components. Control module 88 may provide control signals to indicate how modulation circuit 75 and power conversion circuit 74 are to drive primary coils 76, for instance. For example, control module 88 may control the power with which power conversion circuit 74 drives modulation circuit 75, thereby controlling the power with which primary coil 76 is driven.

Many alternative configurations are possible for both IMD 2 and recharging device 70. For instance, in some embodiments, IMD 2 need not include a telemetry module 59, and/or one or more other logical functions. As another example, various logical functions of IMD 2 and/or recharging device 70 may be partitioned differently. For instance, control module 52 and therapy module 54 of IMD 2 may be combined into a single module, and so on. Thus, the implementations shown in FIG. 2 are to be considered illustrative in nature only.

When a recharge session is initiated by recharging device 70, it may not be possible to receive feedback from IMD 2 concerning the rate at which power is being transferred to IMD 2. This may be the case when rechargeable power source 50 has been depleted to a power level below that which will allow communication to occur via telemetry module 59. Alternatively, telemetry module 59 may be inoperable for another reason. As yet another possibility, IMD 2 may not include a telemetry module 59. In any of these scenarios, recharge must occur in an open-loop recharge mode.

In an open-loop recharge mode, recharging device 70 will not receive feedback to determine the quality of the coupling between primary coil 76 and secondary coil 56. Before continuing, definitions are provided in relation to coupling between primary coil 76 and secondary coil 56.

Manufacturers of rechargeable power sources and/or manufacturers of IMDs that utilize such power sources generally provide specifications that describe recharging of the power sources. For instance, a manufacturer may provide the time that is expected to complete a typical recharge session for a typical patient and/or implant scenario, wherein a typical recharge session recharges the rechargeable power from some lower charge limit to some upper charge limit. The manufacturer generally selects the lower and upper charge limits. The lower charge limit may be selected as a fully-depleted charge state and the upper charge level may be chosen as a fully-charged state, for example. In another example, the lower charge limit may be 20% charged and the upper charge limit may be 80% charged.

The typical time to complete recharge from the lower charge limit to the upper charge limit may be referred to as the "target recharge time". The rate of charge flow to the power source during this typical recharge session may be referred to as the "target charge rate". The average power level that is used by the recharging device to conduct recharge during a typical recharge session may be referred to as the "target power level".

When recharge may be completed from the lower charge limit to the upper charge limit during the target recharge time and at the target power level, good coupling is said to exist between the primary and secondary coil. This is the coupling that is achieved between the primary coil 76 and the secondary coil 56 during a typical recharge session as expected by the manufacturer and experienced by the average user who is in compliance with suggested recharge procedures.

In contrast to good coupling, poor coupling is that coupling that exists when recharge from the lower charge limit to the upper charge limit takes longer than the target recharge time at the target recharge power. The extent of the poor coupling may be expressed in terms of a factor "N", wherein the time required to complete recharge when poor coupling exists is N times the target recharge time. The rate of charge flow to the rechargeable power source 50 during time of poor coupling will be approximately the target charge rate divided by N.

According to the current disclosure, the factor N used to define poor coupling is some value greater than one. N may be a value determined either by a manufacturer of recharging device 70 and/or IMD 2 or a user. The value that is selected for N in defining poor coupling for a given embodiment will depend on the likely uses of the recharger, typical patient compliance, the design of the recharger, and so on. Field strength maps that show magnetic field strength (for near-field coupling) and electromagnetic field strength (for far-field coupling) at various points in three dimensional space may also be used for this purpose, for instance.

In one particular embodiment, N is selected to be "three". In this case, assume that the manufacturer specifies that a target recharge time for a particular type of rechargeable power source is 1 hour. In this case, poor coupling is said to exist when recharging from the lower charge limit to the upper charge limit at the target power level requires at least three hours to complete. In this case, the rate of flow of charge to the rechargeable power source during the recharge session may be approximately one-third that of charge flow during good coupling. Of course, it will be recognized that the target charge time during times of poor coupling (which in this example is three hours) is somewhat of a simplification that does not take into account use of power that may be occurring during the recharge session by the IMD. If power usage during this recharge session is substantial, the rate of flow of charge would have to be somewhat higher than one-third that existing during good coupling in order to complete recharge during three house, since energy is being consumed while recharge is occurring. For purposes of this disclosure, this type of energy usage may be disregarded for simplicity.

In contrast to poor coupling, optimal coupling relates to "best case" coupling between the secondary coil 56 and the primary coil 76. This is the case that corresponds to a scenario wherein the secondary coil is as close as possible to cutaneous boundary 77 of the patient and the primary coil is likewise very close to, or touching, the opposite side of the cutaneous boundary. Moreover, the primary and secondary coils are aligned to substantially share a central axis.

As may be appreciated, the terms "good coupling", "poor coupling", and "optimal coupling" are used to describe the quality of the coupling between the primary coil 76 and the secondary coil 56. Generally, quality of the coupling refers to the amount of the power in the primary coil that is transferred to the secondary coil. Optimal coupling results in the most power transfer from the primary coil to the secondary coil, whereas poor coupling results in the least power transfer. Good coupling results in transfer of power that is somewhere between that achieved by optimal coupling and poor coupling.

With these definitions available for further discussion, use of recharging device 70 in an open-loop recharge mode is considered. In one embodiment of an open-loop recharge mode, power conversion circuit 74 and modulation circuit 75 drive primary coil 76 with a short, high-amplitude pulse that is capable of transferring enough power to secondary coil 56 so that some power will be transferred to rechargeable power source 50 even if coupling is poor. This high-amplitude pulse must be sufficiently short to prevent over-heating of IMD 2 and damage to circuit components even if the high-amplitude pulse is delivered at a time wherein good, or even optimal, coupling exists between the primary coil 76 and secondary coil 56.

Sometime after delivery of the high-amplitude pulse, at a time when circuits within the IMD have cooled to a temperature that will allow for delivery of more power to the IMD, a second low-amplitude pulse is delivered. This low-amplitude pulse has an amplitude that is selected to provide charge to the rechargeable power source 50 assuming good coupling exists between the primary coil 76 and secondary coil 56. The length of this low-amplitude pulse, like that of the high-amplitude pulse, is limited to prevent over-heating of the IMD 2.

Figure 3:
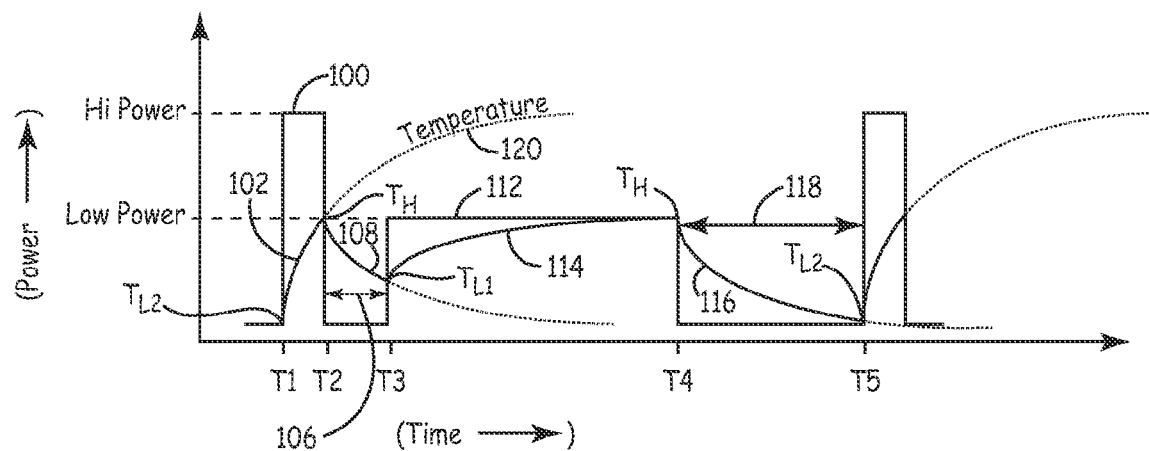
FIG. 3 is a timing diagram illustrating power generated in a secondary coil of an Implantable Medical Device according to one aspect of the disclosure.

FIG. 3 is a waveform diagram illustrating one embodiment of the disclosure. The X axis of this diagram represents time and the Y axis represents amplitude of power through the secondary coil 56.

At time T1, modulation circuit 75 drives interface 84 with a high-power short-duration pulse to primary coil 76. This, in turn, induces a pulse 100 of power in secondary coil 56 having a relatively high amplitude. This high-amplitude power pulse 100 will be provided to charging regulation module 58 to charge rechargeable power source 50.

Coupling between the primary coil 76 and secondary coil 56 may be poor. In this case, the amplitude of power pulse 100 is selected to be sufficiently large to never-the-less likely result in some flow of current to rechargeable power source 50 during the duration of pulse 100.

Because of the high amplitude selected for pulse 100, if coupling is good when this high-amplitude pulse is delivered, it may be necessary to shunt some of the resulting charge away from power source 50. This shunted charge will be dissipated as heat by a shunting element which may be one or more resistors and/or transistors, for example. This shunting operation is necessary because rechargeable power source 50 cannot absorb charge fast enough to utilize all of the charge provided by high-amplitude pulse 100 if this pulse is generated when good or optimal coupling exists between the coils. This is particularly true if rechargeable power source 50 is in a state wherein it has been topped off. As is known in the art, a power source is topped off when it is nearing, or has reached, a full charge, and the power source is in a voltage-limited range of operation. In this state, the rechargeable power source will generally be incapable of receiving a large flow of charge, if it can receive any charge at all.

When shunting of energy occurs during the duration of pulse 100, heating will occur within the IMD, particularly at the shunting element. The resulting rise in temperature during power pulse 100 is represented by waveform segment 102. To prevent overheating of tissue and/or damage to circuit components such as the shunting element, the length of pulse 100 must be selected appropriately so that the temperature does not rise above a pre-selected high-temperature limit $T_H$. Selection of the length of pulse 100 is discussed further below.

At time T2, delivery of pulse 100 is discontinued to prevent over-heating. A first predetermined time delay 106 is then imposed. During this time delay, power is not being transferred to secondary coil 56 and shunting of energy is not needed. Therefore, temperature within IMD 2, and particularly in association with the shunting element, will decrease. This is represented by waveform segment 108. The time delay must be selected to be long enough to allow the temperature to be reduced from the high-temperature limit $T_H$ associated with the high-amplitude pulse 100 to a lower limit $T_{L1}$ that is associated with a subsequent pulse.

When the temperature has been reduced to the lower limit $T_{L1}$ at time T3, modulation circuit 75 again drives primary coil 84 with a low-amplitude longer-duration pulse. This, in turn, induces a power pulse 112 is secondary coil 56 having a relatively low amplitude. This low-amplitude power pulse 112 will be provided to charging regulation module 58 to charge rechargeable power source 50. If coupling between the primary coil 76 and secondary coil 56 is good, the amplitude of power pulse 112 will be sufficiently large to result in a flow of charge to rechargeable power source 50 during the duration of pulse 112. In fact, assuming good coupling, the amount of current that may be absorbed by rechargeable power source 50 during pulse 112 may be higher than that which may be absorbed during the duration of pulse 100. This is because in many cases, rechargeable power source 50 will be able to absorb all or substantially all of the charge resulting from the lower amplitude power pulse 112 because the charge is provided at a lower rate.

There are times when shunting of power will be required even during delivery of the low-amplitude power pulse 112. For instance, this will be necessary when coupling between the primary coil 76 and secondary coil 56 is optimal, and rechargeable power source 50 in a topped-off state. In this type of situation, shunting of at least some, if not all, of the charge will be necessary, resulting in heating of the shunting element. This heating is illustrated by waveform segment 114. Therefore, as was the case with the high-amplitude pulse 100, the duration of power pulse 112 must be limited so that the temperature rise associated with the shunting element is limited to high-temperature limit $T_H$. That is, when the temperature reaches this high-temperature limit at time T4, delivery of power by recharging device 70 to secondary coil 56 must cease so that the shunting element does not overheat. This high-temperature limit may, but need not, be the same as that utilized for the high-amplitude pulse 112.

At time T4, when delivery of energy by recharging device 70 is temporarily discontinued, the temperature associated with the shunting element again decreases from the high-temperature limit associated with the low-amplitude pulse 112, as indicated by waveform segment 116. A second predetermined delay represented by arrow 118 is imposed. This delay is long enough to allow the temperature to be reduced to a second lower limit $T_{L2}$, which occurs at time T5. When this second lower limit $T_{L2}$ is reached, another high-amplitude pulse 120 may be delivered.

In the foregoing manner, the pulse sequence that includes the high-amplitude pulse 100, the first predetermined time delay 106, the low-amplitude pulse 112, and the second predetermined time delay 118 may be repeated any number of times during an open-loop recharge session. In this type of situation, it is important to deliver energy to IMD 2 in a manner that takes into account all scenarios. That is, the pulse train is chosen to likely deliver enough energy so that at least some energy will be transferred to rechargeable power source 50 even in poor coupling scenarios. However, the amplitudes and widths of pulses 100 and 112 must be selected so that if these pulses are delivered during times of good or even optimal coupling, damage to circuit components within the IMD 2 will not result.

Before a more detailed consideration of pulse selection is provided, an example of the circuit of the type that may be used to shunt energy away from rechargeable power source 50 is provided.

Figure 4:
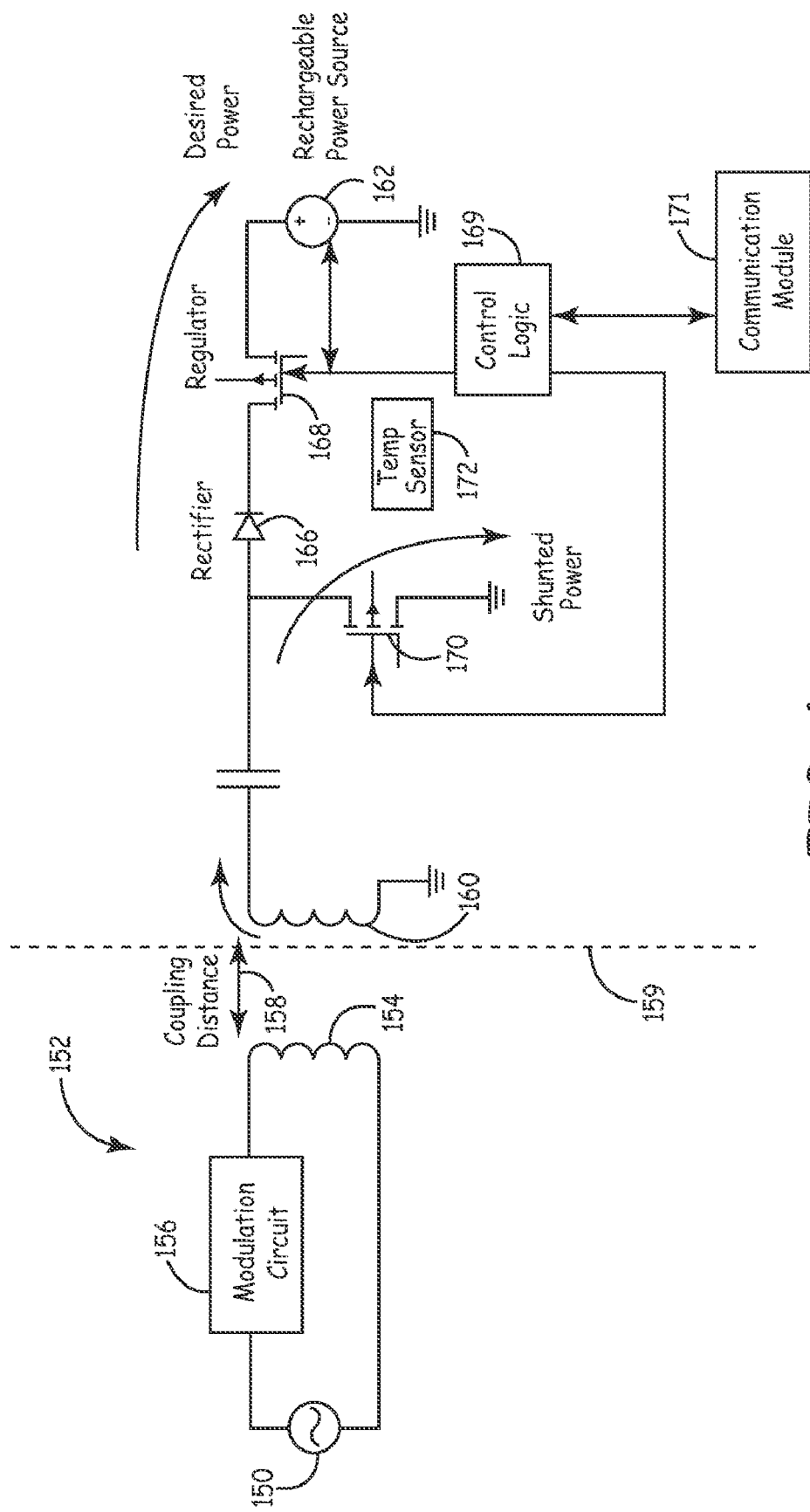
FIG. 4 is a circuit diagram of a system according to one embodiment of the disclosure.

FIG. 4 is a circuit diagram according to one embodiment of the disclosure. In this diagram, a power source 150 in an external recharging device 152 drives primary coil 154 with a power level controlled by modulation circuit 156. Primary coil 154 is separated from secondary coil 160 by a coupling distance 158 that will, at least in part, determine the type of coupling that exists between the primary coil 154 and the secondary coil 160. This will, in turn, determine the amount of charge flowing from secondary coil 160 to the rest of the circuit, including rechargeable power source 162.

According to this disclosure, secondary coil 160 is included within, or otherwise associated with, an IMD such as IMD 2 of FIGS. 1 and 2 or another type of IMD. Secondary coil 160 is on one side of a cutaneous boundary 159 (shown dashed) of a patient and primary coil 154 is on the other side of this boundary. The coupling distance 158 may be determined by the depth of implant of the IMD. The coupling distance 158 may also be determined by the positioning of the primary coil 154 relative to the secondary coil 160.

During recharge when primary coil 154 is coupled to secondary coil 160, power will be transferred to the secondary coil in the manner described above. Before rechargeable power source 162 begins to be topped off, the current flowing from secondary coil 160 is rectified by rectifier 166, which may be a full-wave or half-wave rectification circuit. The rectified current provided by rectifier 166 flows to regulator 168. Control logic 169 operating in conjunction with regulator 168 controls the rate at which charge flows to rechargeable power source 162 to perform recharge. When control logic 169 determines that rechargeable power source 162 is entering a state wherein it is being topped off, control logic 169 signals regulator 168 to decrease the flow of charge to rechargeable power source 162 so that rechargeable power source 162 is not damaged. As rechargeable power source 162 approaches the fully-charged state, regulator 168 substantially halts the flow of charge to rechargeable power source 162 so that an over-charged condition does not result.

If power is being transferred to secondary coil 160 at the same time control logic 169 has reduced or entirely halted the flow of charge that is being provided to rechargeable power source 162, the current produced by secondary coil 160 must be diverted. To do this, control logic 169 enables current to begin flowing through shunting element 170. Shunting element 170 may be a high-power transistor in series with one or more resistors, for example. Other types of shunting elements are available. Such elements are designed to dissipate the current.

The current within shunting element 170 will generate heat. This heat must be limited so that shunting element 170 and the other elements of the circuit attached to secondary coil 160 are not damaged. It is also important to maintain circuit elements at a temperature that does not heat surrounding tissue above a predetermined limit, which may be selected as 41° C., or any other temperature that is considered safe for the patient and will not result in damage to circuit components.

The circuit of FIG. 4 is designed so that if rechargeable power source 162 is in a fully-depleted state, regulator 168 defaults to a state wherein rechargeable power source 162 is accepting current. In this case, shunting element 170 defaults to a disabled state. This allows recharge to take place when no power, or very low power, is being supplied to the various circuit components.

With the foregoing considerations in mind, selection of the various pulses and delays shown in FIG. 3 are considered.

First, selection of the amplitude of the high-amplitude pulse 100 is considered. In one embodiment, this involves first selecting a rate at which charge will be provided to rechargeable power source 162 as a result of the high-amplitude pulse. This selected rate will generally be the minimum flow of charge that is considered useful in recharging rechargeable power source 162. The rate selected for this purpose may depend on the design of the circuit of the IMD, the design of rechargeable power source 162, and the goal associated with receiving this charge. For instance, this minimum rate of charge may be selected based on a goal of re-enabling operation of a communication module 171, which may have been previously disabled because of a low charge level of the rechargeable power source 162.

After this desired rate of charge flow has been selected, the minimum amount of power that must exist within the secondary coil 160 to produce this flow of charge to chargeable power source 162 is determined. This minimum amount of power is determined while shunting element 170 is assumed to be in a disabled state such that all current from secondary coil 160 is assumed to flow to rechargeable power source 162.

The minimum power within secondary coil 160 that will result in the selected flow of charge to rechargeable power source 162 will be dependent on the various components included within the circuit. For instance, the type and configuration of rectifier 166 will affect the power that must be available within secondary coil 160 to result in the selected rate of charge flow to rechargeable power source 162. This power level may be determined theoretically using manufacturing specifications and circuit analysis techniques. Alternatively, the level of power that is required within secondary coil 162 to generate the selected charge flow to rechargeable power source may be determined empirically, as by varying power levels within secondary coil 160 and determining the power level that is required to achieve a rate of charge flow to the rechargeable power source.

After the required power level in the secondary coil 160 is determined, the primary coil 154 is positioned so that poor coupling exists between the primary coil 154 and the secondary coil 160. As discussed above, what is considered to be poor coupling may be varied based on the embodiment in use, and will depend on selection of some multiplier N used to quantify poor coupling relative to good coupling.

With the primary coil 154 and the secondary coil 160 oriented relative to one another so that poor coupling exists, the amount of power with which modulation circuit 156 must drive primary coil 154 to obtain the desired power level (that is, the power level needed to obtain the desired current flow) within secondary coil 160 is determined. This will be the amount of power which will be used by modulation circuit 156 to generate the high-amplitude pulse 100. In other words, this will determine the amplitude of the high-amplitude pulse in the primary coil.

Next, the width of pulse 100 is determined. As previously described, pulse 100 cannot be so wide that heating will occur that will damage circuit components such as shunting element 170. Such heating will be the largest during a limiting condition. In one embodiment, this limiting condition comprises a scenario involving optimal coupling between primary coil 154 and secondary coil 160 at a time when control logic 169 has discontinued the flow of current to rechargeable power source 162 because this power source has been topped off. During this limiting condition, all of the energy from the high-amplitude pulse 100 will be dissipated as heat by shunting element 170. The pulse width must be limited to prevent damage as a result of this heat.

To emulate this type of scenario, primary coil 154 may be positioned so that it is optimally, or nearly optimally, coupled to the secondary coil 160. To further emulate an implant scenario, secondary coil 160 and the circuit to which it is coupled may be enclosed in a hermetically-sealed IMD, which is submerged in a gelled saline bath that is maintained at approximately 37° C. to emulate the temperature and consistency of living tissue.

While the primary coil 154 and secondary coil 160 are aligned in the foregoing manner, and with control logic 169 configuring shunting element 170 to shunt all of the power received by secondary coil 160, modulation circuit 156 drives primary coil 154 with the previously-determined amount of power needed to generate the high-amplitude pulse 100.

While this power level is being generated within primary coil 154, the temperature of shunting element 170 is monitored. This may be accomplished using a temperature sensor 172 that is positioned in proximity to shunting element 170. Such a sensor may include one or more diodes, thermocouples or proportional-to-absolute-temperature (PTAT) sensors, for instance.

Sampling of the temperature as the previously-determined amount of power is delivered will result in a temperature waveform similar to that shown as waveform segment 102 (FIG. 3) and additional waveform segment 120 (shown dashed). This temperature waveform will have a shape described by the following equation:

$$T_t = T_f + (T_i - T_f)e^{\frac{-t}{\tau}}$$ Equation 1

In Equation 1, $T_i$ is the initial temperature before power is delivered to secondary coil 160, which in the current example is the ambient temperature of 37° C. This may be the temperature of the gelled saline bath in one type of emulation environment. Temperature $T_f$ is the final equilibrium temperature that will be reached as modulation circuit 156 continues to drive primary coil 154 at the power level associated with the high-amplitude pulse 100. At this equilibrium temperature $T_f$, an equilibrium condition will be achieved wherein the energy being added to the system equals that lost as heat such that the temperature is no longer rising. This will be the temperature at which waveform segment 120 will eventually "flatten out" so that temperature is neither rising nor falling. Finally, temperature $T_t$ is the instantaneous temperature measured at any time t during the monitoring process.

In the foregoing manner, temperature values may be measured and/or otherwise determined for $T_i$ and $T_f$. By substituting in these values for $T_i$ and $T_f$ into Equation 1 and by further substituting in a measured value $T_t$ obtained at time t, the value for $\tau$ may be derived. This value $\tau$ is the temperature coefficient of the system. In one embodiment, $\tau$ will primarily depend on the temperature response of shunting element 170, since the temperature measurements are being performed by temperature sensor 172 that is in close proximity to shunting element 170, and since shunting element 170 is generating the large majority of the heat within the IMD in a system wherein the shunting element defines the limiting condition. The value $\tau$ may also be affected somewhat by the way in which the various circuit elements of the IMD are packaged and the type of heat sinking capabilities that are provided.

Next, the desired temperature at the start and end of pulse 100 must be selected. The temperature at the start of pulse 100 may be selected as the ambient temperature (in this example, 37° C.) or a temperature that is something other than ambient temperature. Generally, this will be the temperature of a living body in which IMD 2 will be implanted. The temperature at the end of the pulse must be selected to be something higher than that selected for the start of pulse 100 since the temperature of shunting element 170 will rise during delivery of pulse 100. In one embodiment, the temperature selected for the end of pulse 100 will be the maximum temperature that shunting element 170 should be allowed to reach. This temperature may be chosen according to manufacturing specification for instance. In FIG. 3, this temperature is shown as the high-temperature limit $T_H$ that is measured at time T2.

Next, the times associated with the selected temperatures $T_{L2}$ and $T_H$ may be determined. For instance, the selected temperature $T_{L2}$ for the start of pulse 100 may be substituted as $T_t$ in Equation 1. The previously determined values for $T_i$, $T_f$, and $\tau$ may likewise be substituted into Equation 1. The equation may then be solved for t. This process may be repeated for the temperature selected for the end of pulse 100 to determine at which time temperature $T_H$ will occur.

The foregoing calculations will yield times $Time_{L2}$ and $Time_H$, which are the times at which the shunting element will reach temperatures $T_{L2}$ and $T_H$, respectively. By subtracting $Time_H$ from $Time_{L2}$, the width of pulse 100 may be determined.

It may be appreciated that the pulse width may also be determined simply by consulting the temperature waveform obtained while sampling temperature, as represented by waveform segments 102 and 120 of FIG. 3. From this waveform, the times at which temperatures $T_{L2}$ and $T_H$ are reached may be determined, and the interval between these two times may likewise be determined. This is the maximum pulse width that will ensure that the temperature of the shunting element does not exceed $T_H$ if the limiting condition occurs.

In a manner similar to that described above for the high-amplitude pulse 100, the desired pulse amplitude and width of pulse 112 may be determined. To determine amplitude of this pulse, a second desired rate of charge flow to rechargeable power source is selected. For instance, this second rate of charge flow may be a maximum rate at which charge may be absorbed by rechargeable power source 162 when this power source is not in a topped-off state. In yet another embodiment, this rate may be the maximum rate at which rechargeable power source 162 may absorb charge when the power source is not in a topped-off state and that further promotes power source longevity. Alternatively, the selected flow rate may be the maximum rate at which rechargeable power source 162 may absorb charge before this power source reaches some upper charge limit, such as 80% of charge.

Once the desired flow of charge to power source 150 has been selected, the amplitude of power within secondary coil 160 that will produce this charge flow may be determined. This may be accomplished empirically using measurements and observations. For instance, power within the secondary coil 160 may be varied as the rate of charge flow to the power source is measured. Alternatively, the determination may be made using manufacturer specifications, circuit modeling techniques and/or theoretical calculations.

Next, the power level with which primary coil 154 must be driven to generate the desired power in secondary coil 160 is determined. In one embodiment, this determination is made by positioning primary coil 154 so that good coupling is achieved between the primary coil 154 and secondary coil 160. The power level within primary coil 154 may be varied to determine that needed to generate the required power level within secondary coil.

The width of pulse 112 may next be determined. For this determination, it will be assumed that a limiting condition exists. For this embodiment, the limiting condition comprises optimal coupling between the primary and secondary coils, as well as a rechargeable power source 162 that is in a topped-off state, as was the case above. In this type of situation, all power generated in secondary coil 160 is being shunted by shunting element 170.

To emulate this limiting condition, primary coil 154 is positioned to be optimally-coupled to secondary coil 160 in the manner described above. As previously described, this involves minimizing the distance between the two coils and allowing the two coils to substantially share a central axis. After control logic 169 disables regulator 168 and enables shunting element 170, modulation circuit 156 drives primary coil 154 with the power level associated with low-amplitude pulse 112.

While the power level associated with the low-amplitude pulse is being delivered, the temperature of shunting element 170 is sampled over time. A temperature waveform for the low-amplitude pulse 112 is obtained, which is represented by waveform 114. In the manner described above, this waveform will exhibit a shape described by Equation 1. In this equation, temperature $T_i$ is the initial temperature before power is delivered to secondary coil 160. This may be 37° C., for example, if this is the ambient temperature of the system. Temperature $T_f$ is the final equilibrium temperature that will be reached as modulation circuit 156 continues to drive primary coil 154 with the power level associated with the low-amplitude pulse 112 and temperature stabilizes such that it is neither increasing nor decreasing.

Next, in the manner described above for the high-amplitude pulse, the low-amplitude pulse width may be obtained. As previously discussed, this may be determined directly using the derived waveform 114. Alternatively, this may be accomplished by substituting a temperature selected for the beginning or the end of pulse 112 into Equation 1 (e.g., $T_{L1}$ or $T_H$) into the equation along with the values for $T_i$ and $T_f$ determined above. The same value for τ that was determined above in reference to pulse 100 may further be substituted into Equation 1. Performing this analysis for both $T_{L1}$ and $T_H$ will yield the times at which these two temperatures occur, allowing derivation of the pulse width to be completed.

After the amplitudes and widths of pulses 100 and 112 have been determined, the desired time delays between pulses may be determined. For instance, to determine the length of the first delay of FIG. 3 illustrated by arrow 106, a sampling of temperature could continue after power is no longer being delivered to the primary coil 154. During this time, temperature will decrease, since secondary coil 160 is not receiving power. The temperature samples will correspond to waveform segment 108. To determine size of delay 106, waveform segment 108 may be used to determine the length of time required for the temperature to drop from the high-temperature limit $T_H$ to the first lower limit of $T_{L1}$. A similar approach may be used to determine the second delay indicated by arrow 118. In this exemplary embodiment, the size of this delay will be that associated with a temperature drop from $T_H$ to the second lower limit of $TL_2$.

In another embodiment, Equation 1 set forth above may be used to determine the size of the delays. In the case, the same value may be used for τ that was determined in any of the ways described above. The value for $T_i$ is the temperature existing when power is first removed from the secondary coil, which for either delay is high-temperature limit $T_H$ in this embodiment, although $T_H$ could be different for the two pulses if desired. The value for $T_f$ is the temperature to which cooling will continue if power is not re-supplied, which in this case may be the ambient temperature of approximately 37° C. Finally, the value for $T_t$ may be supplied. This will be the temperature to which cooling is to be allowed to continue until power is re-supplied. In the case of the first delay associated with arrow 106, the first lower limit $T_{L1}$ will be substituted for this purpose. In the case of the second delay associated with arrow 118, the second lower limit $T_{L2}$ will be substituted for this purpose. Making respective substitutions and solving for time t will yield the size of the delay.

In the foregoing manner, amplitude and width of each of the pulses 100 and 112 may be determined. The durations of the delays that will be used to facilitate the desired cooling between these pulses may also be determined. As previously discussed, such calculations will be system-specific, depending on the circuit design of the IMD, the configurations of the primary coil 154 and secondary coil 160, and on the design of the circuit included in the external recharging device 152.

As previously noted, while the pulse sequence shown in FIG. 3 represents power pulses generated within secondary coil 160, a similar pulse sequence must be generated within primary coil 154 to obtain that shown in FIG. 3 in the secondary coil 160. That is, a pulse having a same or similar pulse width as that shown in FIG. 3 will be generated in primary coil 154 to obtain the high-amplitude pulse 100 in the secondary coil 160. Similarly, a pulse having a same or similar pulse width as that shown in FIG. 3 will be generated in primary coil 154 to obtain the low-amplitude pulse 112 in the secondary coil 160. Moreover, for a given coupling efficiency, the amount of power required to generate a corresponding pulse in the primary will be proportional to the amplitude of the power pulse in the secondary coil 160. The specific power levels needed to drive primary coil 154 are determined in the manner described above. Finally, the size of delays required in the primary coil will be the same, or similar to, those delays in the primary coil 154.

While the pulses shown in FIG. 3 are depicted as having rise and fall times that approach zero, this need not be the case. In a circuit having a quality factor, or Q, greater than 1, the rise and fall times may be non-zero such that the pulses exhibit some degree of "rounded" edges.

Those skilled in the art will appreciate that other embodiments are possible within the scope of the disclosure. For instance, the foregoing assumes that temperature rises within shunting element 170 will be the limiting factor in determining durations of the pulses. In another system, this may not be the case. For instance, heating of the surrounding enclosure containing the circuit of FIG. 4 (e.g., the can of IMD 2), and the associated heating of surrounding tissue may be the limiting factor in some cases. In these instances, one or more temperature sensors 172 may be thermally-coupled to the inside or the exterior surface of the can when performing temperature monitoring to determine pulse widths. The temperature of one or more other components may be monitored instead of, or in addition to, those described above.

In other types of systems, more heat may be dissipated when the rechargeable power source is receiving charge than when the rechargeable power source is nearly-charged or fully-charged and shunting is occurring. In these types of systems, the limiting condition involves charging of the power source rather than the shunting operation. Thus, temperature sensors may be thermally-coupled to or otherwise associated with the rechargeable power source 162 to monitor temperature when this power source is receiving charge during whichever state is known to produce the most heat (e.g., before the rechargeable power source is approaching the topped-off state, or some other state).

In still other scenarios, the limiting condition may involve the temperature of secondary coil 160, or some other component of the system. Temperature measurements obtained in association with this limiting condition will be utilized to determine pulse widths in a manner similar to that described above.

While the foregoing examples discussed the signal pulse within the secondary coil as being a power pulse, it may be noted that the signal may alternatively be thought of as current pulse or a voltage pulse. Of course, in this case, it is important to remember that power transferred to the secondary coil 160 is proportional to the square of the current in that coil or the square of the voltage across the coil, and heat dissipation is proportional to power transfer. Temperature rise will not be directly proportional to the current or voltage level that is selected for the pulse amplitude.

It will be noted that the system shown in FIG. 4 is merely exemplary. Many types of circuit configurations may be used for the recharging device 152 as well as the circuit that is coupled to the secondary coil 160 for recharging the rechargeable power source 162. Many embodiments are possible within the scope of the disclosure.

Figure 5:
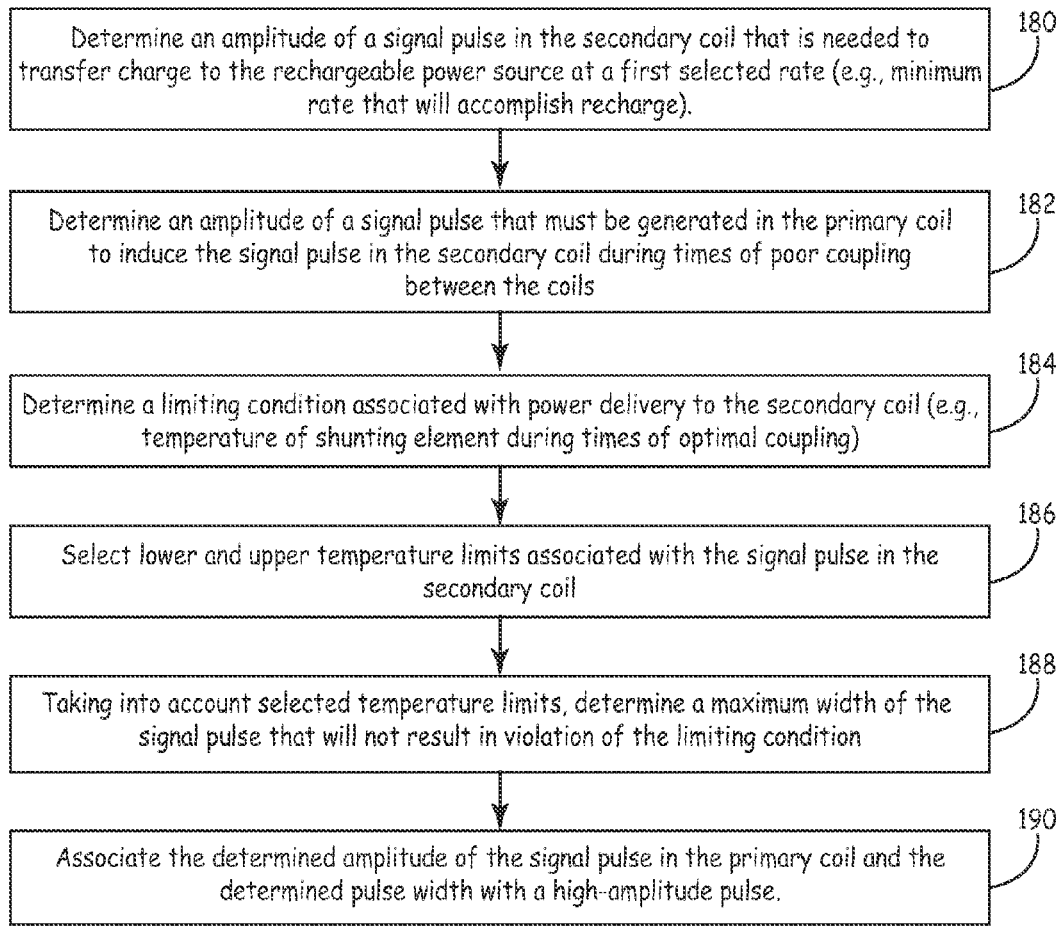
FIG. 5 is a flow diagram according to one embodiment of determining pulse amplitudes and widths.

FIG. 5 is a flow diagram of one method according to the current disclosure. This flow diagram illustrates one method for determining a pulse width and amplitude needed to generate a high-amplitude pulse such as the high-amplitude pulse 100 of FIG. 3. First, a determination is made concerning the amplitude of a signal pulse in the secondary coil that will result in the transfer of charge to the rechargeable power source at a first predetermined rate. For example, it may be determined what amplitude of a power pulse is needed in the secondary coil 160 to produce a minimum flow of charge to the rechargeable power source 162 that will accomplish recharge. Any other selected rate of charge may be selected in the alternative.

Next, an amplitude of a signal pulse that must be generated in the primary coil to induce the signal pulse in the secondary coil during times of poor coupling between the coils is determined (182). The definition of poor coupling is as set forth above. This determination as to pulse amplitude may be made theoretically or empirically.

A limiting condition associated with power delivery to the secondary coil may be determined (184). For instance, in the foregoing examples, the limiting condition was assumed to be the temperature of shunting element 170 during times of optimal coupling between the primary coil 154 and secondary coil 160 when the rechargeable power source 162 is in a fully-charged state. Other limiting conditions may exist in other types of systems, as discussed above, and may involve temperature of the rechargeable power source, temperature of the secondary coil, and so on.

Lower and upper temperature limits associated with the signal pulse in the secondary coil 160 may further be selected (186). For instance, in reference to high-amplitude pulse 100, the lower and upper limits are the second lower limit $T_{L2}$ and the upper limit $T_H$, respectively, that are shown in FIG. 3. Various temperature limits may be selected for this purpose. Generally, the lower limit will be a temperature at, or exceeding the ambient temperature (e.g., the temperature of a living body) and the upper temperature limit will be a maximum temperature considered acceptable for the monitored condition (e.g., maximum temperature that should be allowed for the shunting element based on limits of the shunting element and safety limits for the surrounding tissue.). Other limits may be used in the alternative.

Taking into account the selected temperature limits, a determination is made concerning the maximum width of the signal pulse generated in the secondary coil that will not result in violation of the limiting condition (188). The amplitude associated with the pulse in the primary coil and the pulse width determined in step 188 may then be associated with a high-amplitude pulse (190). These parameters may be used to generate a high-amplitude pulse in a primary coil that will induce a corresponding high-amplitude pulse in a secondary coil.

It may be noted that various aspects of the method of FIG. 5 may be programmable. For instance, a user may be allowed to select the first rate of charge used to determine the pulse amplitude in step 180. As another example, a user may also be allowed to select the limiting condition and/or the high and low-temperature limits used to determine pulse widths. Additionally or alternatively, the user may be allowed to select the value used for N that determines when poor coupling exists. As noted above, in one embodiment, N is set to three. In another embodiment, N is any integer or non-integer positive value greater than one. Thus, a user may be allowed to exercise some control over the manner in which open-loop recharge occurs.

Figure 6:
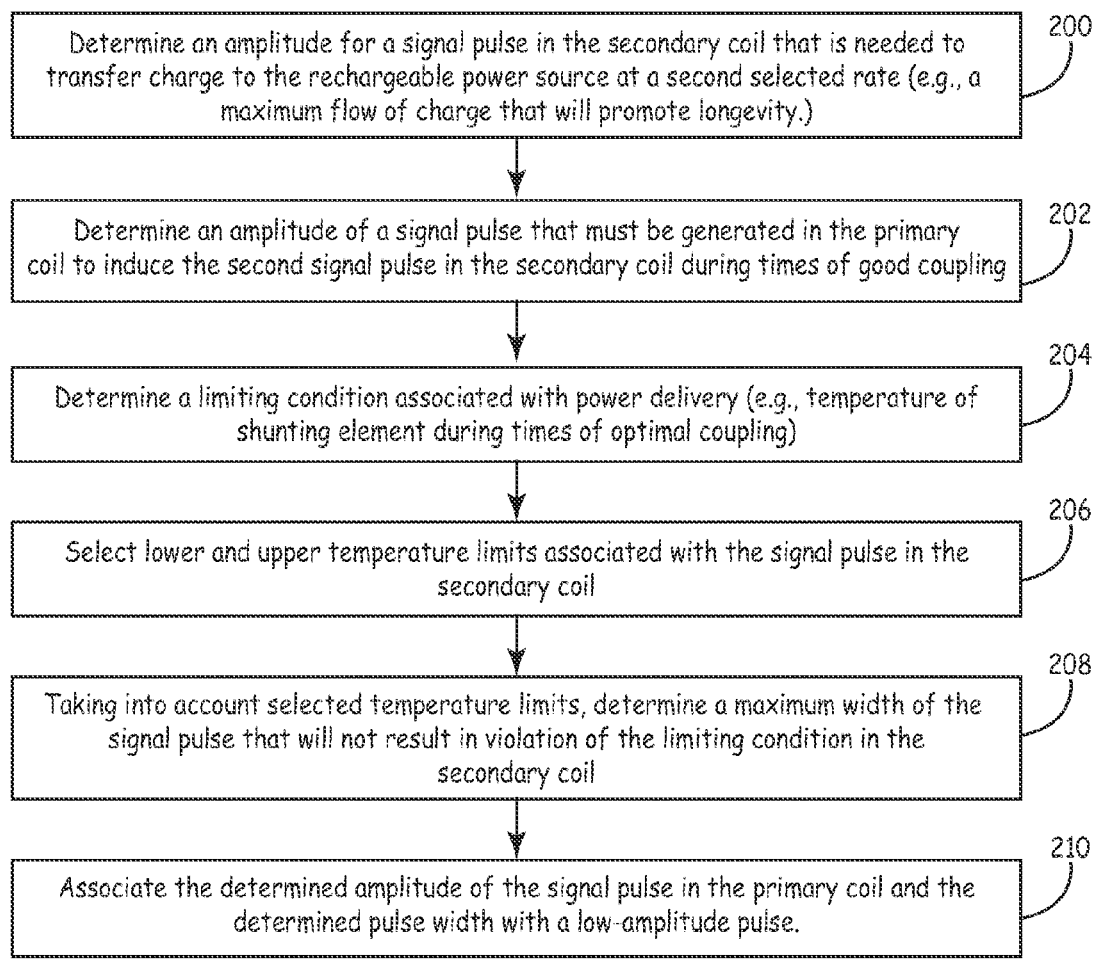
FIG. 6 is a flow diagram according to another embodiment of determining pulse amplitudes and widths.

FIG. 6 is a flow diagram of another method according to the current disclosure. This flow diagram illustrates one method for determining a pulse width and amplitude needed to generate a low-amplitude pulse such as low-amplitude pulse 112 of FIG. 3. First, an amplitude is selected for a signal pulse in the secondary coil that will transfer charge to the rechargeable power source at a second selected rate (200). For example, this second selected rate may be the amplitude of a current pulse in the secondary coil 160 that will result in a maximum flow of charge that may be received by rechargeable power source 162 during a time when rechargeable power source has not yet been topped off. Optionally, this rate may be selected as that maximum rate that will promote longevity of the power source. Any other selected rate of charge may be selected in the alternative.

Next, an amplitude of a signal pulse that must be generated in the primary coil to induce the signal pulse in the secondary coil during times of good coupling between the coils is determined (202). The definition of good coupling is as set forth above. This determination as to the amplitude of the second signal pulse may be made theoretically or empirically.

Next, a limiting condition associated with power delivery to the secondary coil may be determined (204). As previously discussed, in the foregoing examples, the limiting condition was assumed to be the temperature of shunting element 170 during times of optimal coupling between the primary coil 154 and secondary coil 160 when the rechargeable power source 162 is in a fully-charged state. Other limiting conditions may exist in other types of systems, as discussed above.

Lower and upper temperature limits associated with the signal pulse in the secondary coil 160 may further be selected (206). For instance, in reference to low-amplitude pulse 112, the lower and upper limits are the first lower limit $T_{L1}$ and the upper limit $T_H$, respectively, that are shown in FIG. 3. Various temperature limits may be selected for this purpose. Generally, the lower limit will be a temperature at, or above the ambient temperature (e.g., the temperature of a living body). The upper temperature limit will be the maximum temperature considered allowable for the monitored condition (e.g., maximum temperature that should be allowed for the shunting element based on limits of the shunting element and safety limits for the surrounding tissue.).

Taking into account the selected temperature limits, a determination is made concerning the maximum width of the signal pulse generated in the secondary coil that will not result in violation of the limiting condition (208). The amplitude associated with the primary coil pulse and the determined pulse width may then be associated with a low-amplitude pulse (210). These parameters may be used to generate a low-amplitude pulse in a primary coil that will induce a corresponding low-amplitude pulse in a secondary coil.

As was the case above regarding the method of FIG. 5, various aspects of the method of FIG. 6 may be programmable. For instance, a user may be allowed to select the second rate of charge used to determine the second pulse amplitude in step 200. As another example, a user may also be allowed to select the limiting condition and/or the high and low-temperature limits used to determine pulse widths. The value of N used to determine poor coupling may likewise be selected, although it should be understood that the same selected value of N and the same limiting condition must be used when determining amplitude and widths of both low- and high-amplitude pulses. In the foregoing manner, a user may be allowed to exercise some control over the manner in which operation occurs.

Figure 7:
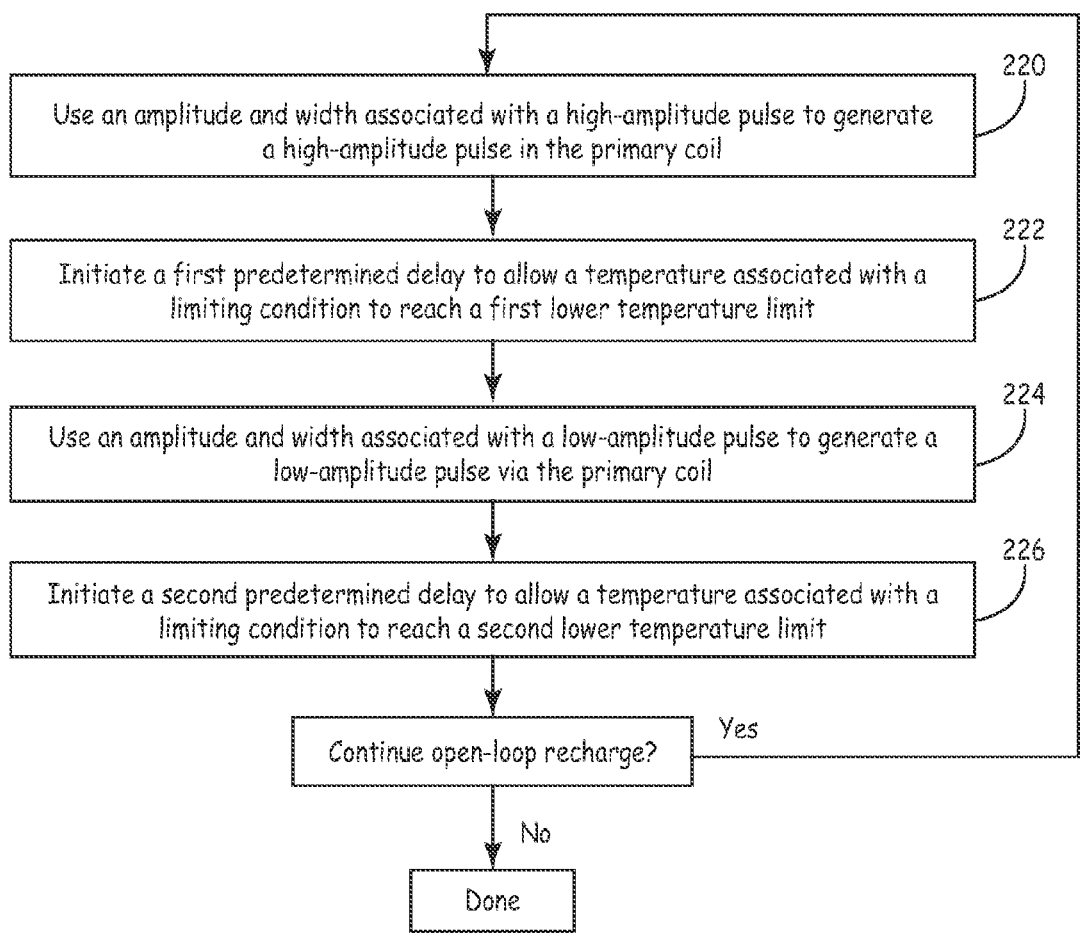
FIG. 7 is a flow diagram of delivering pulses according to one embodiment.

FIG. 7 is a flow diagram of yet another method according to the current disclosure. An amplitude and pulse width associated with a high-amplitude pulse is used to generate a high-amplitude pulse in the primary coil (220). A first predetermined delay is initiated to allow a temperature associated with a limiting condition to reach a first lower temperature limit (222). For instance, in FIG. 3, the temperature associated with shunting element 170 is allowed to transition from $T_H$ to $T_{L1}$ during the delay illustrated by arrow 106.

Next, an amplitude and pulse width associated with a low-amplitude pulse is used to generate a low-amplitude pulse in the primary coil (224). A second predetermined delay is initiated to allow a temperature associated with a limiting condition to reach a second lower temperature limit (226). For instance, in FIG. 3, the temperature associated with shunting element 170 is allowed to transition from $T_H$ to $T_{L2}$ during the delay illustrated by arrow 118. If recharge is to continue in the open-loop manner according to this method (228), processing returns to step 220. Otherwise, processing is considered complete (230). In one embodiment, the determination of step 228 as to whether to continue to perform open-loop recharge may be made by receiving input from a user. Additionally or alternatively, this determination may be made by using a timer, with recharge being discontinued after a predetermined amount of time. This predetermined amount of time may be programmable.

In one embodiment, recharge in the open-loop manner is discontinued upon receiving communication from IMD 2 (e.g., as via a telemetry uplink communication), indicating that the rechargeable power source 162 has received enough charge to sustain a communication session with the external device. In this case, recharge may transition to a closed-loop mode wherein the IMD provides information concerning coupling efficiency and/or the battery state. In this mode, the external recharging device can control power transmission associated with the primary coil based on this information.

The foregoing provides one example of determining pulse widths and amplitudes of high-amplitude and low-amplitude pulses for use in performing recharge in an open-loop manner. Other methods are available for determining amplitudes and pulse widths. For instance, in one alternative embodiment, the amplitude of the high-amplitude pulse with which the primary coil is driven is selected as the maximum amplitude with which the recharging device is capable of driving the primary coil, and without regard to the rate of charge flow to the rechargeable power source 162. Thus, in this embodiment, steps 180 and 182 (FIG. 5) may be eliminated as unnecessary. The width of the high-amplitude pulse in this alternative embodiment may be determined in a manner similar to that described in reference to steps 184-190 of FIG. 5.

In another embodiment, the amplitude of the low-amplitude pulse may be selected based on some percentage of the amplitude selected for use with the high-amplitude pulse when the high-amplitude pulse is selected according to techniques of the foregoing paragraph. For instance, the amplitude may be selected as fifty percent of that of the high-amplitude pulse. When using this type of approach, steps 200 and 202 (FIG. 6) may be eliminated. The remaining steps of FIG. 6 may be performed to determine the width of the low-amplitude pulse.

In yet another embodiment, a selection of distances may be utilized as a surrogate for poor coupling and good coupling. For instance, in this case, good coupling may be assumed to be that associated with a first selected coupling distance 158 (FIG. 4), and poor coupling may be assumed to be that coupling associated with a second selected coupling distance. As one example, the first (shorter) distance may be the typical distance used by an average patient assuming average patient compliance. The second (longer) distance associated with poor coupling may be some multiple D of the first distance, or may be selected in another manner. For instance, this longer distance may be selected using statistical analysis of patient compliance data. These approaches are described in reference to FIGS. 8 and 9, as follows.

Figure 8:
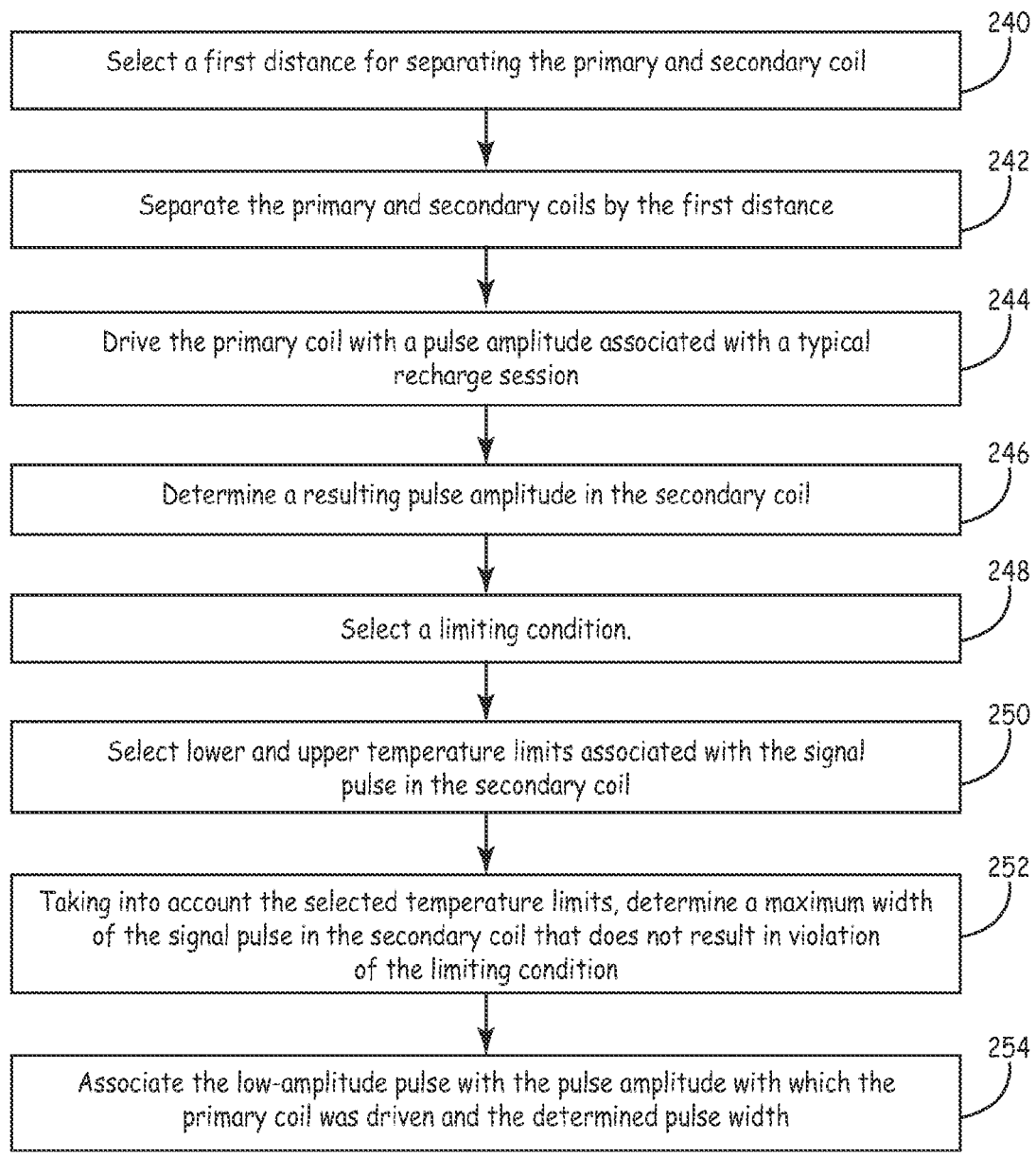
FIG. 8 is a flow diagram illustrating a method of determining pulse amplitudes and widths based on a coupling distance between a primary and secondary coil.

FIG. 8 is one method of using distances as a surrogate for coupling quality to determine a pulse amplitude for a low-amplitude pulse. A first coupling distance is selected for use in determining a low-amplitude pulse (240). This may be a distance separating primary and secondary coils during a typical recharge session based on patient compliance data, for instance. The primary coil 154 is positioned so that it is separated from the secondary coil 160 based on this first coupling distance (242). The primary coil is driven at a power level associated with a typical recharge session, which may be that associated with good coupling, as discussed above. This power level may be based on patient data and/or manufacturer specifications (244). While the primary coil is driven at this power level, a determination is made regarding the amplitude of the resulting signal pulse in the secondary coil (246). A limiting condition is selected (248). Upper and lower temperature limits associated with a low-amplitude signal pulse in the secondary coil may be determined (250). Taking into account the selected temperature limits, a maximum width of the pulse in the secondary coil that does not result in violation of the limiting condition may be determined (252). The amplitude employed in step 244 to drive the primary coil and the pulse width determined in step 252 is associated with the low-amplitude pulse. (254).

Figure 9:
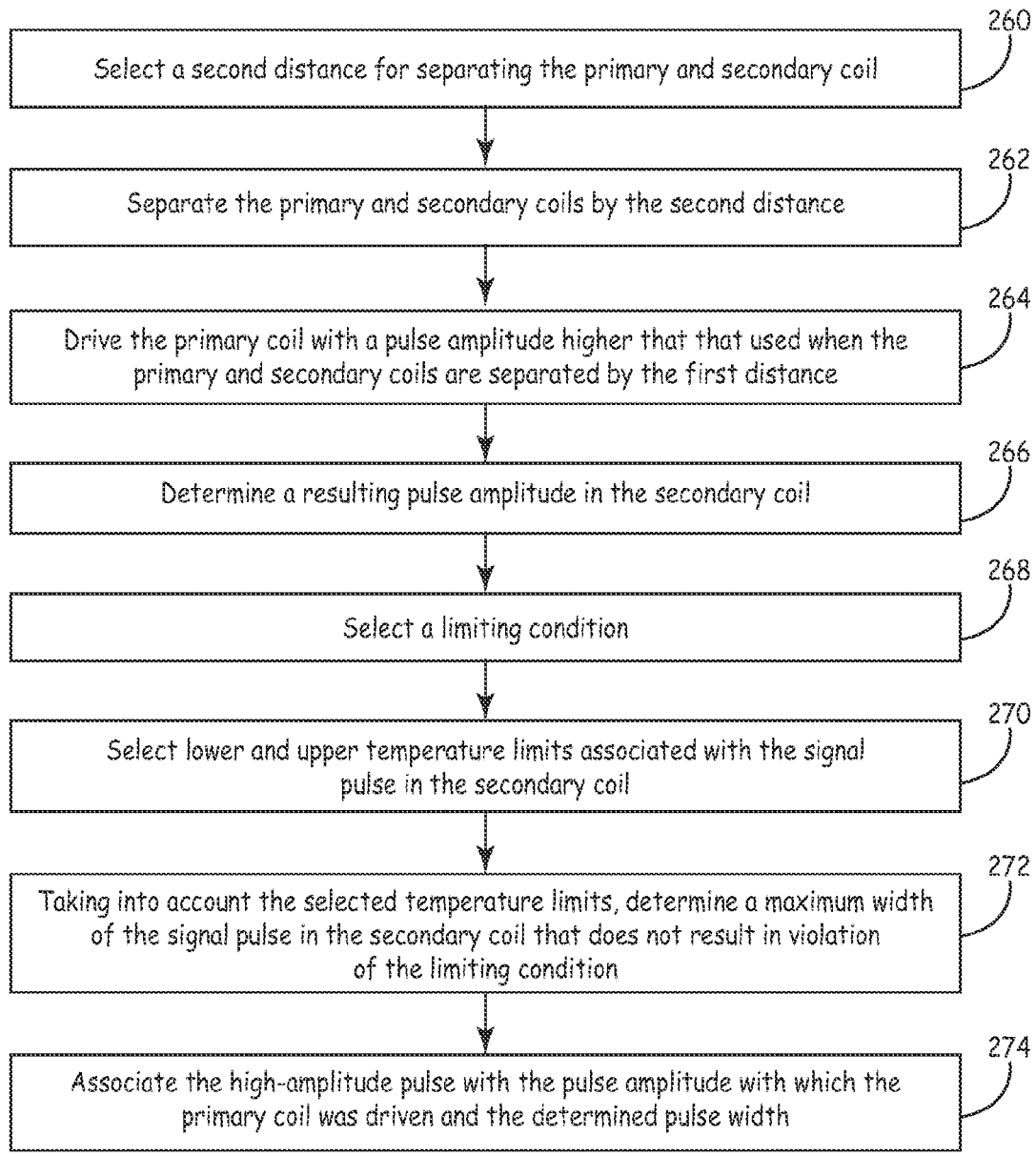
FIG. 9 is flow diagram illustrating another method of determining pulse amplitudes and widths based on a coupling distance between a primary and secondary coil.

FIG. 9 is one method of using distances as a surrogate for coupling quality to determine a pulse amplitude for a high-amplitude pulse. A second coupling distance is selected for use in determine a high-amplitude pulse (260). This may be a distance that is some multiple D of the first distance employed in FIG. 8 above, or may be some other distance greater than the first distance. The primary coil 154 is positioned so that it is separated from the secondary coil 160 based on this second coupling distance (262). The primary coil is driven at a selected amplitude that is higher than that used when determining the low-amplitude pulse (264). This amplitude may likewise be based on the multiple D if desired, although this is not necessary. For instance, primary coil may be driven at a power level that is D times that used in driving the primary coil to determine the amplitude of the low-amplitude pulse.

While the primary coil is driven at the selected amplitude, a determination is made regarding the amplitude of the resulting pulse in the secondary coil (266). A limiting condition is selected (268). Upper and lower temperature limits associated with a high-amplitude signal pulse in the secondary coil may be determined (270). Taking into account the selected temperature limits, a maximum width of the signal pulse in the secondary coil that does not result in violation of the limiting condition may be determined (272). The amplitude employed in step 264 to drive the primary coil and the pulse width determined in step 272 is associated with the high-amplitude pulse. (274).

In yet another embodiment, some combination of the methods used in FIGS. 5 and 9 may be used to determine the amplitude and width of the high-amplitude pulse. For instance, step 180 (FIG. 5) may be performed to select a desired pulse amplitude in the secondary coil for the high-amplitude pulse. The coils may then be positioned according to the second distance of step 260 (FIG. 9) for the high-amplitude pulse. The pulse amplitude with which the primary coil must be driven to achieve this desired pulse amplitude is determined, and the remaining steps 184-190 of FIG. 5 may be completed.

In a similar manner, some combination of the methods of FIGS. 6 and 8 may be used to determine the amplitude and width of the low-amplitude pulse. For instance, step 200 (FIG. 6) may be performed to select a desired pulse amplitude in the secondary coil for the low-amplitude pulse. The coils may then be positioned according to the first distance of step 240 (FIG. 8). The pulse amplitude with which the primary coil must be driven to achieve this desired pulse amplitude in the secondary coil is determined, and the remaining steps 204-210 of FIG. 6 may be completed.

As may be appreciated, many methods exist for selecting the amplitudes of the high-amplitude and low-amplitude pulses. What is important is that once the amplitudes are selected, the widths and inter-pulse delays are selected so as not to violate a selected limiting condition. Thus, many embodiments of methods and systems are available for use in practicing the techniques described herein. The mechanisms discussed herein are to be considered exemplary and not limiting, with the disclosure limited only by the claims that follow.

What is claimed is:

1. A system, comprising:
a secondary coil implantable within a living body;
a rechargeable power source; and
a recharging device external to the living body configured to induce in an open-loop manner a sequence of pulses in a primary coil that is coupled to the secondary coil, wherein the recharging device is not receiving feedback associated with recharging the rechargeable power source, the sequence including high-amplitude pulses alternating with low-amplitude pulses, each high-amplitude pulse having an amplitude selected to result in transfer of charge to the rechargeable power source during times of poor coupling between the primary coil and the secondary coil, each low-amplitude pulse having an amplitude selected to result in transfer of charge to the rechargeable power source during times of good coupling between the primary coil and the secondary coil, and wherein the sequence of pulses is selected to prevent violation of a limiting condition associated with recharging the rechargeable power source when recharging occurs in the open-loop manner.

2. The system of claim 1, wherein the amplitude of the high-amplitude pulses is selected to transfer charge to the rechargeable power source at a selected minimum rate when coupling between the primary coil and the secondary coil is poor.

3. The system of claim 1, wherein the rechargeable power source is configured to receive charge at a maximum rate when the rechargeable power source is not topped off, and wherein the amplitude of the low-amplitude pulses is selected based on the maximum rate at which the rechargeable power source is configured to receive charge when the rechargeable power source is not topped off.

4. The system of claim 1, wherein at least one of the amplitude of the high-amplitude pulses and the amplitude of the low-amplitude pulses is selected based on a selected coupling distance between the primary coil and the secondary coil.

5. The system of claim 1, wherein the amplitude of the high-amplitude pulses is selected based on a maximum power level available to the recharging device to drive the primary coil.

6. The system of claim 1, wherein at least one of the width of the high-amplitude pulses and the width of the low-amplitude pulses is selected to prevent violation of the limiting condition.

7. The system of claim 6, wherein at least one of the width of the high-amplitude pulses and the width of the low-amplitude pulses is selected based on at least one of a low-temperature limit and a high-temperature limit.

8. The system of claim 1, further comprising a shunting element coupled to shunt the flow of charge away from the rechargeable power source, and wherein the limiting condition comprises an amount of heat generated in the shunting element when optimal coupling exists between the primary coil and the secondary coil and while flow of substantially all charge from the secondary coil is directed through the shunting element.

9. The system of claim 1, wherein a delay exists between each high-amplitude pulse and a subsequent low-amplitude pulse, the delay being the minimum time required to allow a temperature that is associated with the limiting condition to transition from a high-temperature limit associated with the end of the high-amplitude pulse to a low-temperature limit associated with the beginning of the subsequent low-amplitude pulse.

10. The system of claim 9, wherein a second delay exists between each low-amplitude pulse and a subsequent high-amplitude pulse, the second delay being the minimum time required to allow a temperature that is associated with the limiting condition to transition from a high-temperature limit associated with the end of the low-amplitude pulse to a low-temperature limit associated with the beginning of the subsequent high-amplitude pulse.

11. The system of claim 1, further comprising an implantable medical device to carry the secondary coil and the rechargeable power source.

12. The system of claim 1, further comprising a communication module, and wherein the sequence of pulses is discontinued after the rechargeable power source contains enough charge to allow the communication module to communicate with the recharging device.

13. A system to recharge a rechargeable power source of an implantable medical device (IMD), comprising:

a power source;
a primary coil configured to wirelessly couple to a secondary coil of the IMD; and
a control unit configured to cause the power source to drive the primary coil with high-amplitude pulses and low-amplitude pulses in an open-loop manner without receiving feedback associated with recharging the rechargeable power source, each high-amplitude pulse followed by a low-amplitude pulse and each low-amplitude pulse followed by a high-amplitude pulse, each high-amplitude pulse being of an amplitude selected to cause the secondary coil to provide charge to the rechargeable power source when poor coupling exists between the primary coil and the secondary coil, each low-amplitude pulse being of an amplitude selected to cause the secondary coil to provide charge to the rechargeable power source when good coupling exists between the primary coil and the secondary coil.

14. The system of claim 13, wherein a limiting condition exists that limits how the rechargeable power source may be recharged, and wherein at least one of the width of the high-amplitude pulses and the width of the low-amplitude pulses is selected so that violation of the limiting condition does not occur.

15. The system of claim 14, wherein at least one of the width of the high-amplitude pulses and the width of the low-amplitude pulses is selected based on a lower temperature limit and a high-temperature limit selected in association with the limiting condition.

16. The system of claim 13, wherein a limiting condition exists for recharging the rechargeable power source, and wherein the control unit imposes a first time delay between each high-amplitude pulse and a following low-amplitude pulse, the first time delay being of a minimum length required to allow a transition from a high limit associated with the high-amplitude pulse to a low limit associated with the following low-amplitude pulse to be completed.

17. The system of claim 16, wherein the control unit imposes a second time delay between each low-amplitude pulse and a following high-amplitude pulse, the second time delay being of a minimum length required to allow a transition from a high limit associated with the low-amplitude pulse to a low limit associated with the following high-amplitude pulse to be completed.

18. The system of claim 13, wherein the control unit continues to cause the power source to drive the primary coil with the high-amplitude pulses and the low-amplitude pulses for a predetermined period of time.

19. A system, comprising:
an implantable medical device (IMD) having a secondary coil and a rechargeable power source to receive charge from the secondary coil; and
a recharging device having a primary coil and a circuit configured to drive the primary coil with a sequence of pulses to perform open-loop recharge of the rechargeable power source, the sequence of pulses including high-amplitude pulses alternating with low-amplitude pulses, each high-amplitude pulse being of a relatively high amplitude, each low-amplitude pulse being of a relatively low amplitude, and wherein none of the low-amplitude pulses and none of the high-amplitude pulses cause violation of a limiting condition that limits the manner in which the rechargeable power source may be recharged.

20. The system of claim 19, further including a shunting element, and wherein the limiting condition comprises a temperature limit reached during optimal coupling of the primary coil with the secondary coil when substantially all charge from the secondary coil is directed to the shunting element.

21. The system of claim 19, wherein the width of each of the low-amplitude pulses and each of the high-amplitude pulses is selected based on a temperature coefficient associated with the limiting condition.

22. The system of claim 21, wherein at least one of the amplitude of the high-amplitude pulses and the amplitude of the low-amplitude pulses is selected based on a desired rate of charge flow to the rechargeable power source.

23. The system of claim 21, wherein at least one of the amplitude of the high-amplitude pulses and the amplitude of the low-amplitude pulses is selected based on a selected coupling distance between the primary coil and the secondary coil.

24. The system of claim 21, wherein at least one of the amplitude of the high-amplitude pulses and the amplitude of the low-amplitude pulses is selected based on a selected power level employed by the recharging device to generate the sequence of pulses.

25. A method, comprising:
wirelessly coupling a primary coil external to a living body to a secondary coil implantable in the living body; and
generating, via the coupling, a sequence of pulses in the secondary coil for use in recharging a rechargeable power source, the sequence including high-amplitude pulses and low-amplitude pulses, the high-amplitude pulses each having an amplitude selected to deliver a flow of charge to the rechargeable power source when the coupling is of a first quality, the low-amplitude pulses each having an amplitude selected to deliver a flow of charge to the rechargeable power source when the coupling is of a second quality that is better than the first quality, and wherein the width of the high-amplitude pulses and the low-amplitude pulses is selected to prevent violation of a limiting condition during open-loop recharge of the rechargeable power source.

26. The method of claim 25, further including selecting at least one of the amplitude of the high-amplitude pulses and the amplitude of the low-amplitude pulses based on a selected rate of charge flow to the rechargeable power source needed to recharge the rechargeable power source during a recharge session having a selected quality of coupling.

27. The method of claim 25, further including selecting at least one of the amplitude of the high-amplitude pulses and the amplitude of the low-amplitude pulses based on a respective coupling distance between the primary coil and the secondary coil.

28. The method of claim 25, further comprising:
(a) generating one of the high-amplitude pulses;
(b) initiating a first predetermined delay that is selected based on the limiting condition;
(c) after the first predetermined delay, generating one of the low-amplitude pulses;
(d) initiating a second predetermined delay that is selected based on the limiting condition; and
repeating steps (a), (b), (c) and (d) one or more times.

29. The method of claim 28, wherein the steps are repeated for a predetermined period of time.

30. The method of claim 28, wherein the steps are repeated until the rechargeable power source reaches a predetermined charge level.

31. The method of claim 25, further comprising:
selecting at least one low-temperature limit associated with the limiting condition;
selecting at least one high-temperature limit associated with the limiting condition;

determining a temperature coefficient associated with the limiting condition; and determining at least one of the width of the high-amplitude pulses and the width of the low-amplitude pulses based on the at least one low-temperature limit, the at least one high-temperature limit and the temperature coefficient.

* * * * *